US006432411B1

(12) United States Patent
Ivy et al.

(10) Patent No.: US 6,432,411 B1
(45) Date of Patent: Aug. 13, 2002

(54) RECOMBINANT ENVELOPE VACCINE AGAINST FLAVIVIRUS INFECTION

(75) Inventors: John Ivy, College Station, TX (US); Gary Bignami, Honolulu, HI (US); Michael McDonell, Bogart, GA (US); David E. Clements, Honolulu, HI (US); Beth-Ann G. Coller, Woluwe Saint Lambert (BE)

(73) Assignee: Hawaii Biotechnology Group, Aiea, HI (US)

( * ) Notice: Subject to any disclaimer, the term of this patent is extended or adjusted under 35 U.S.C. 154(b) by 0 days.

(21) Appl. No.: 09/352,387

(22) Filed: Jul. 13, 1999

(51) Int. Cl.[7] ................................................ A61K 39/12

(52) U.S. Cl. ................................ 424/218.1; 424/186.1; 424/279.1; 424/283.1

(58) Field of Search ........................... 424/218.1, 186.1, 424/283.1, 279.1

(56) References Cited

U.S. PATENT DOCUMENTS

| | | | | | |
|---|---|---|---|---|---|
| 5,139,776 | A | * | 8/1992 | Chazono et al. | 424/92 |
| 5,494,671 | A | * | 2/1996 | Lai et al. | 424/218.1 |
| 5,679,354 | A | * | 10/1997 | Morein et al. | 424/278.1 |
| 6,136,561 | A | * | 10/2000 | Ivy et al. | 435/69.3 |
| 6,165,477 | A | * | 12/2000 | Ivy et al. | 424/218.1 |

FOREIGN PATENT DOCUMENTS

| | | |
|---|---|---|
| EP | 0884056 A | 12/1998 |
| FR | 2 741 077 A | 5/1997 |
| WO | WO 96/37221 A | 11/1996 |
| WO | WO 98/50556 A | 11/1998 |
| WO | WO 99/06068 | 2/1999 |
| WO | WO 00/12128 | 3/2000 |

OTHER PUBLICATIONS

Bernard et al., Recombinant protein expression in a Drosophila cell line: comparison with the baculovirus system. Cytotechnology 15 (1–3) pp. 139–144, 1994.*

Baldridge et al., Effective adjuvants for the induction of antigen–specific delayed–type hypersensitivity. Vaccine 15(4):395–401, 1997.*

Kamstrup, S. et al., "Production of a highly immunogenic subunit ISCOM vaccine against Bovine Viral Diarrhea Virus," (1999) VACCINE 17:1057–1064.

Yeolokar, L. et al., "Preparation and characterization of immunostimulating complexes (ISCOMs) of Japanese encephalitis virus," (1996) VACCINE 14 (6): 1553–1559.

* cited by examiner

*Primary Examiner*—Donna C. Wortman
(74) *Attorney, Agent, or Firm*—Morrison & Foerster LLP

(57) ABSTRACT

A vaccine contains at least one Drosophila cell-secreted, recombinantly-produced form of a truncated Flavivirus envelope glycoprotein, as an active ingredient, and an adjuvant, as a critical component of the vaccine. The adjuvant is an immunomodulating agent having an iscom-like structure and comprising within the iscom-like structure at least one lipid and at least one saponin, and a pharmaceutically acceptable vehicle. Such a vaccine protects a subject against infection by a Flavivirus.

7 Claims, 14 Drawing Sheets

Anti-DEN2 HMAF

SEQUENCE LISTING

```
<160> NUMBER OF SEQ ID NOS: 6

<210> SEQ ID NO 1
<211> LENGTH: 46
<212> TYPE: DNA
<213> ORGANISM: Flavivirus sp.

<400> SEQUENCE: 1
```

-continued

```
cttctagatc tcgagtaccc gggaccatgc gctgcatagg aatatc                46


<210> SEQ ID NO 2
<211> LENGTH: 35
<212> TYPE: DNA
<213> ORGANISM: Flavivirus sp.

<400> SEQUENCE: 2

gctctagagt cgactattat cctttcttga accag                            35


<210> SEQ ID NO 3
<211> LENGTH: 47
<212> TYPE: DNA
<213> ORGANISM: Flavivirus sp.

<400> SEQUENCE: 3

attctagatc tcgagtaccc gggaccatgt ttcatctgac cacacgc               47


<210> SEQ ID NO 4
<211> LENGTH: 37
<212> TYPE: DNA
<213> ORGANISM: Flavivirus sp.

<400> SEQUENCE: 4

tctctagagt cgactattag gcctgcacca taactcc                          37


<210> SEQ ID NO 5
<211> LENGTH: 42
<212> TYPE: DNA
<213> ORGANISM: Flavivirus sp.

<400> SEQUENCE: 5

atgggagcca gatctcgagt acccgggacc atgtttggat aa                    42


<210> SEQ ID NO 6
<211> LENGTH: 13
<212> TYPE: PRT
<213> ORGANISM: Flavivirus sp.

<400> SEQUENCE: 6

Met Gly Ala Arg Ser Arg Val Pro Gly Thr Met Phe Gly
  1               5                  10
```

RECOMBINANT ENVELOPE VACCINE AGAINST FLAVIVIRUS INFECTION

TECHNICAL FIELD

The invention relates to vaccines designed to protect against flaviviral disease. More specifically, the invention concerns recombinant envelope (E) glycoprotein produced in cellular production systems and formulated with modern adjuvants that are shown to maximize 1) induction of high titer virus neutralizing antibodies believed to be important in protection against infection and 2) provide protection of immunized animals from virulent viral challenge.

BACKGROUND ART

The family Flaviviridae includes the family prototype yellow fever virus (YF), the four serotypes of dengue virus (DEN-1, DEN-2, DEN-3, and DEN-4), Japanese encephalitis virus (JE), Tick-borne encephalitis virus (TBE), and about 70 other disease causing viruses. Flaviviruses are small, enveloped viruses containing a single, positive-strand RNA genome. The envelope of flaviviruses is derived from the host cell membrane and is decorated with virally-encoded transmembrane envelope proteins. The E glycoprotein, which is the largest viral structural protein, contains functional domains responsible for cell surface attachment and intraendosomal fusion activities. It is also a major target of the host immune system, inducing virus neutralizing antibodies and protective immunity, as well as antibodies which inhibit hemagglutination.

Although flavivirus transmission and the pathology of infection are quite varied among the different viruses, Dengue viruses serve as an illustrative example of the family. Dengue viruses are transmitted to man by mosquitoes of the genus Aedes, primarily *A. aegypti* and *A. albopictus*. The viruses cause an illness manifested by high fever, headache, aching muscles and joints, and rash Some cases, typically in children, result in a more severe form of infection, dengue hemorrhagic fever/dengue shock syndrome (DHF/DSS), marked by severe hemorrhage, vascular permeability, or both, leading to shock Without diagnosis and prompt medical intervention, the sudden onset and rapid progression of DHF/DSS can be fatal.

Dengue viruses are the most significant group of arthropod-transmitted viruses in terms of global morbidity and mortality with an estimated one hundred million cases of dengue fever occurring annually including 250,000 to 500,000 cases of DHF/DSS (Rigau Perez et al., 1998; Gubler, 1998). With the global increase in population, urbanization of the population especially throughout the tropics, and the lack of sustained mosquito control measures, the mosquito vectors of dengue have expanded their distribution throughout the tropics, subtropics, and some temperate areas, bringing the risk of dengue infection to over half the world's population. Modern jet travel and human emigration have facilitated global distribution of dengue serotypes, such that multiple serotypes of dengue are now endemic in many regions. Accompanying this there has been an increase in the frequency of dengue epidemics and the incidence of DHF/DSS in the last 15 years. For example, in Southeast Asia, DHF/DSS is a leading cause of hospitalization and death among children (Hayes and Gubler, 1992).

The flaviviral genome is a single, positive-strand RNA molecule, approximately 10,500 nucleotides in length containing short 5' and 3' untranslated regions, a single long open reading frame, a 5' cap, and a nonpolyadenylated 3' terminus. The complete nucleotide sequence of numerous flaviviral genomes, including all four DEN serotypes and YF virus have been reported (Fu et al., 1992; Deubel et al, 1986; Hahn et al, 1988; Osatomi et al., 1990; Zhao et al, 1986; Mackow et al., 1987; Rice et al., 1985). The ten gene products encoded by the single open reading frame are translated as a polyprotein organized in the order, capsid (C), premembrane/membrane (prM/M), envelope (E), nonstructural protein (NS) 1, NS2a, NS2b, NS3, NS4a, NS4b, and NS5 (Chambers, et al. 1990). Processing of the polyprotein is initiated cotranslationally, and full maturation requires both host and virally-encoded proteases. The sites of proteolytic cleavage in the YF virus have been determined by comparing the nucleotide sequence and the amino terminal sequences of the viral proteins. Subsequent to initial processing of the polyprotein, prM is converted to M during viral release (Wengler, and Wengler, 1989) and anchored C is processed during virus maturation (Nowak and Wengler, 1989).

While all dengue viruses are antigenically related, antigenic distinctions exist which define the four dengue serotypes. Infection of an individual with one serotype provides long-term immunity against reinfection with that serotype but fails to protect against infection with the other serotypes. In fact, immunity acquired by infection with one serotype may potentially enhance pathogenicity by other dengue serotypes. This is particularly troubling as secondary infections with heterologous serotypes have become increasingly prevalent as the virus has spread, resulting in the co-circulation of multiple serotypes in many geographical areas and increased numbers of cases of DHF/DSS (Rigau Perez et al., 1998; Gubler, 1998). Halstead (1982) demonstrated that anti-dengue antibodies can augment virus infectivity in vitro, and proposed that serotype crossreactive, non-neutralizing antibodies to E enhance infection in vivo, resulting in DHF/DSS (Halstead, 1981). This viewpoint is not however, universally accepted (Rosen, 1989). In particular the dengue gene product which may be responsible for the enhanced pathogenesis remains the subject of some debate. For example, it has been proposed that dengue serotype-crossreactive $CD4^+$ CD8-cytotoxic T cells (CTLs) specific for NS3 may contribute to the pathogenesis of DHF/DSS by producing IFN-γ and by lysing dengue virus-infected monocytes (Kurane et al., 1991; Okamoto et al., 1998; Mathew et al., 1998). Recent evidence demonstrating that CTLs specific for E are not serotype-crossreactive may suggest that use of E subunit vaccines would not induce the potentially harmful cross-reactive CTL response (Livingston et al., 1994). Other studies have suggested a potential role for NS1 in DHF/DSS (Falconer, 1997). Regardless of the mechanism for enhanced pathogenicity of a secondary, heterologous dengue infection, strategies employing a tetravalent vaccine should avoid such complications. Helpful reviews of the nature of the dengue disease, the history of attempts to develop suitable vaccines, structural features of flaviviruses in general, as well as the structural features of the envelope protein of flaviviruses are available (Halstead 1988; Brandt 1990; Chambers et al., 1990; Mandl et al., 1989; Henchal and Putnak, 1990; Putnak 1994; Rey et al., 1995; Rigau Perez et al., 1998; Gubler, 1998; Cardosa, 1998).

Although many approaches to dengue vaccines have been pursued, there is no acceptable vaccine currently available. While a significant amount of effort has been invested in developing candidate live-attenuated dengue vaccine strains, the strains tested to date have proven unsatisfactory (see, e.g., Eckels et al, 1984; Bancroft et al, 1984; McKee et al, 1987). Despite this limited success, live attenuated candidate vaccine strains continue to be developed and tested (Hoke et al, 1990; Bhamarapravati et al, 1987; Dharakul et al., 1994; Edelman et al., 1994; Angsubhakorn et al., 1994; Vaughn et al., 1996). The construction of several full-length infectious flavivirus clones (Rice et al., 1989; Lai et al., 1991; Sumiyoshi et al., 1992; Kapoor et al., 1995; Polo et al., 1997; Kinney et al., 1997; Gualano et al., 1998) has facilitated studies aimed at identifying the determinants of virulence in flaviviruses (Bray and Lai, 1991; Chen et al., 1995; Kawano et al., 1993; Cahour et al., 1995; Men et al., 1996; Hiramatsu et al., 1996; Pryor et al., 1998; Lai et al., 1998; Gualano et al., 1998; Valle and Falgout, 1998). While these studies remain quite preliminary and little information on virulence has been obtained, the cDNA clones derived from these studies are being used as a backbone for development of recombinant chimeric dengue vaccine strains (Bray and Lai, 1991; Chen et al., 1995; Bray et al., 1996; Lai et al., 1998). However, all of the live virus vaccine approaches remain plagued by difficulties in developing properly attenuated strains and in achieving balanced, tetravalent formulations.

Similarly, efforts to develop killed dengue vaccines have met with limited success. Primarily these studies have been limited by the inability to obtain adequate viral yields from cell culture systems. Virus yields from insect cells such as C6/36 cells are generally in the range of $10^4$ to $10^5$ pfu/ml, well below the levels necessary to generate a cost-effective killed vaccine. Yields from mammalian cells including LLC-MK2 and Vero cells are higher, but the peak yields, approximately $10^8$ pfu/ml from a unique Vero cell line, are still lower than necessary to achieve a truly cost-effective vaccine product.

In the absence of effective live attenuated or killed dengue vaccines, a significant effort has been invested in the development of recombinant, dengue subunit or viral-vectored vaccines. Many of the vaccine efforts that use a recombinant DNA approach have focused on the E glycoprotein. This glycoprotein is a logical choice for a subunit vaccine as it is key to viral biology and the host immune response to the virus. The E glycoprotein is exposed on the surface of the virus, binds to the cell receptor, and mediates fusion (Chambers et al., 1990; Chen et al., 1996). It has also been shown to be the primary target for the neutralizing antibody response. Monoclonal antibodies directed against purified flaviviral E proteins are neutralizing in vitro and some have been shown to confer passive protection in vivo (Henchal et al., 1985; Heinz et al., 1983; Mathews et al., 1984; Kimuro-Kuroda and Yasui, 1988).

Although the primary amino acid sequence of flaviviral E glycoproteins are variable (45–80% identity), all have twelve conserved cysteine residues, forming six disulfide bridges, and nearly superimposable hydrophilicity profiles suggesting that they probably have similar secondary and tertiary structures. Recently, the structure of a soluble fragment of the tick-borne encephalitis (TBE) virus envelope glycoprotein was solved at 2 Å resolution (Rey et al., 1995). Coordinate synthesis of prM and E appears to be important to obtain the native conformation of E. Expression of E in the absence of prM may result in a recombinant product that presents a different set of epitopes than those of the native virion (Konishi and Mason 1993; Heinz et al, 1994; Matsuura et al, 1989). Epitope mapping of the E expressed with prM suggests that the co-expressed protein more closely resembles the native virus. As prM and E appear to form heterodimers during viral maturation and E undergoes an acid pH-induced conformational change, Heinz et al (1994) has suggested the association of prM and E is required to prevent irreversible pH-induced conformational changes during transit through the secretory pathway. However, it has been shown that carboxy-truncated forms of flavivirus E expressed in the absence of prM elicit protection from challenge (Men et al, 1991; Jan et al, 1993; Coller et al., unpublished data), suggesting expression of E in the absence of prM can result in the display of protective epitopes.

Recombinant dengue E glycoproteins have been expressed in several heterologous expression systems to date (See Putnak, 1994 and Chambers et al., 1997 for recent reviews). In general the systems have proven unsatisfactory for production of a cost-effective dengue vaccine due to limitations in antigen quality, quantity, or both. The following paragraphs highlight the major dengue recombinant subunit vaccine efforts and summarize the results obtained to date.

Most efforts using *Escherichia coli* have yielded poor immunogen incapable of eliciting protective responses. This probably reflects non-native conformation of dengue proteins expressed by bacteria and the necessity to process the viral proteins through the secretion pathway in order to achieve proper disulfide bond formation and glycosylation. While initial tests in mice suggested some level of efficacy (Srivastava et al., 1995; Mason et al., 1990), subsequent testing in primates failed to confirm the efficacy (R. Putnak, personal communication). Recently, fusion of a gene fragment encoding amino acids 298–400 (B domain) of the DEN-2 virus envelope was expressed as a fusion protein with the *E. coli* maltose binding protein (Simmons et al., 1998). This fusion protein conferred only partial protection to mice against challenge infection with a lethal dose of DEN-2 virus again demonstrating the limited efficacy of *E. coli* expressed products. Work in our laboratory has confirmed that recombinant products expressed in *E. coli* do not induce dengue specific immune responses in mice.

Use of the eukaryotic yeast expression systems *Saccharomyces cerevisiae* and *Pichia pastoris* for expression of dengue E has also proved to be less than desirable in terms of the quantities of immunogenic recombinant product obtained. Work in our laboratory has demonstrated that the expression levels of dengue E achieved in these systems are well below that which would be required to produce a cost-effective dengue vaccine. Work in other laboratories has suggested that the system may be useful for the production of virus-like particles (Sugrue et al., 1997). However, again the expression levels are quite low and the neutralizing antibody titer induced by the recombinant product is very low (1:10; Sugrue et al., 1997). This is despite the fact that the expression systems have been reported to be very efficient for heterologous expression of a variety of recombinant products (Cregg et al., 1993).

Use of the baculovirus expression system for flavivirus subunit vaccine production has also met with limited success (Reviewed in Putnak, 1994). In contrast to the high expression levels reported for various heterologous proteins in the baculovirus system, the levels of expression of flavivirus structural proteins were only moderate (Deubel et al., 1991; Staropoli et al., 1997). In addition, reactivity against a panel of anti-flaviviral monoclonal antibodies (MAbs) indicated that many conformationally sensitive epitopes were not present (Deubel et al., 1991). This suggests that folding of recombinant E produced in the baculovirus system may differ from the natural viral E protein. Furthermore, immunization with baculovirus-expressed recombinant envelope protein from DEN-1 (Putnak et al., 1991), DEN-4 (Eckels et al., 1994), DEN-2/DEN-3 hybrid (Bielefeldt-Ohmann et al., 1997), Japanese Encephalitis virus (McCown et al., 1990), or Yellow Fever virus (Despres et al., 1991) failed to elicit substantial titers of virus neutralizing antibodies or protection against viral challenge. Recently, Staropoli et al. (1997) were able to show neutralizing antibodies and some protection in mice using affinity-purified DEN-2 envelope as an immunogern. The truncated envelope glycoprotein was modified at the C-terminus with six-histidine amino acid residues (His6 tag) in place of the last 100 amino acids. However, this product induced only moderate neutralizing antibody titers and showed only partial protection in primates (Velzing et al., 1999).

Several reports have described vaccinia-flavivirus recombinants expressing envelope proteins as part of a polyprotein. The most consistently successful results in vaccinia expression of flaviviral proteins have been obtained co-expressing prM and E. Mice immunized with recombinant vaccinia expressing Japanese Encephalitis (JE) virus prM and AE developed higher neutralizing antibody titers and survived higher challenge doses of virus (>10,000 $LD_{50}$; Konishi et al, 1992) than mice immunized with recombinant vaccinia virus expressing E alone (>10 $LD_{50}$; Mason et al, 1991). Similarly, mice immunized with a vaccinia-Yellow Fever (YF) virus recombinant expressing prM-E were protected from virus challenge at levels equivalent to that of the attenuated YFV-17D vaccine, while vaccinia-YF virus recombinants expressing E-NS1, C-prM-E-NS1, or NS1 failed to protect mice (Pincus et al, 1992). Vaccinia-DEN-1 recombinants expressing prM-E elicited neutralizing and hemagglutination inhibiting antibodies in mice, while recombinants expressing DEN-1 C-prM-E-NS1-NS2a-NS2b elicited no E-specific immune response (Fonseca et al, 1994). The lack of recent advances in this technology have mainly been associated with the limited utility and problems associated with the use of vaccinia vectors for human immunization.

Use of the mammalian expression system based upon the Chinese hamster ovary (CHO) cell line to express dengue virus E has also been disappointing. Efforts in our laboratory and others has shown that although this is a very useful expression system for production of a variety of recombinant products (Bebbington and Hentschel, 1987; Cockett et al., 1990; Kaufman et al., 1985; Kaufman, 1990), DEN-2 E is not expressed efficiently. Intracellular expression levels of DEN-2 80%E were ≦100 ng/ml and secretion was undetectable.

Thus, while many heterologous expression systems have been developed and shown to be effective for production of certain recombinant products, not all expression systems are effective for producing all recombinant products. In fact, despite the fact that a system may be reported to be effective for production of one recombinant protein, predictions on efficacy of expression of other recombinant products do not always hold. In particular, efficient expression of conformationally relevant recombinant flavivirus E has remained elusive. As described above a wide variety of expression systems ranging from bacterial, fungal, and insect to mammalian systems have failed to efficiently produce conformationally relevant flavivirus E in significant quantities, highlighting the highly empirical nature of efficient heterologous gene expression.

Within the last ten years an alternative eukaryotic expression system that uses the *Drosophila melanogaster* Schneider 2 (S2) cell line has been developed and used to efficiently express the envelope glycoprotein of Human Immunodeficiency Virus (Ivey-Hoyle et al., 1991; Culp et al, 1991; van der Straten et al, 1989). The inventions embodied herein make use of the Drosophila S2 system to produce recombinant flavivirus subunit polypeptides (specified by example are dengue and Japanese encephalitis E subunits), and have found the system can readily produce 20–50 mg of recombinant protein per liter of medium (unpublished). The recombinant product we have focused most of our efforts on is a soluble form of E, which is truncated at the carboxy-terminal end resulting in a polypeptide that represents approximately 80% of the full-length E molecule (amino acids 1–395; 80%E). We have expressed 80%E as a single open-reading frame with prM to enhance proper folding and secretion as described above. The expression levels achieved using this combination of expression system and recombinant DNA construct (20–50 mg/l) far exceed those achieved in other systems thus providing a cost-effective source of flavivirus antigen for vaccine production. In addition, we have demonstrated that the recombinant 80%E product secreted by these cells is conformationally relevant in that it binds to conformationally sensitive monoclonal antibodies and induces high titer virus neutralizing antibodies in mice and monkeys (Coller et al., in preparation).

Adjuvants are materials that increase the immune response to any given antigen. The addition of immune stimulating compounds to vaccines was first described in 1925 (Ramon, 1925). Since then a number of adjuvants have been developed, but currently only calcium and aluminum salts are licensed for use in human vaccine products. Although these adjuvants are sufficient for some vaccines, numerous studies have demonstrated that other adjuvants are significantly more efficacious for inducing both humoral and cellular immune responses and may be required to induce a protective response. Some of these, including Freund's complete adjuvant (FCA) and Quil A, have been shown to be quite effective adjuvants in animals. However, they have significant toxicities or side-effects which make them unacceptable for human and veterinary vaccines. In fact, even aluminum hydroxide has recently been associated with the development of injection site granulomas in animals, raising safety concerns about its use. Because of these problems significant efforts have been invested in developing potent adjuvants which lack the undesirable side effects of adjuvants like FCA.

A number of modern adjuvant formulations have been developed and show significant promise, especially in combination with recombinant products. Several of these modern adjuvants are being tested in preclinical and clinical trials designed to examine both efficacy and safety. Several recent reviews summarize the approaches being used to develop modern adjuvants for human vaccines (Cox and Coulter, 1997; Gupta and Siber, 1995; Hughes and Babiuk, 1994). As described in these reviews there are five major modes of action of adjuvants; immunomodulation, presentation, induction of cytotoxic cellular responses, targeting, and depot generation. Various adjuvant formulations target different modes of action resulting in varying responses within the immunized animals. The specific formulation which is optimal for any given vaccine may be predicted based upon the disease target and desired response. However, often the optimal formulation must be determined empirically.

Adjuvants may be classified in a number of ways (Cox and Coulter, 1997; Gupta and Siber, 1995; Hughes and Babiuk, 1994). In broad terms there are two major categories, particulate and non-particulate. Included in the particulate category are aluminum salts, calcium salts, water-in-oil emulsions, oil-in-water emulsions, immune stimulating complexes (iscom) and iscom matrices, liposomes, nano- and microparticles, proteosomes, virosomes, stearyl tyrosine, and γ-Inulin. Non-particulate adjuvants include muramyl dipeptide (MDP) and derivatives (e.g. threonyl MDP, murametide, etc.), non-ionic block copolymers, saponins (e.g. Quil A and QS21), lipid A or its derivative 4' monophosphoryl lipid A (MPL), trehalose dimycolate (TDM), various cytokines including γ-interferon and interleukins 2 or 4, carbohydrate polymers, derivatized polysaccharides (e.g. diethylaminoethyl dextran), and bacterial toxins (e.g. cholera toxin or *E. coli* labile toxin). Often modern adjuvant formulations are combinations of various components designed to maximize specific immune responses.

The literature describing the use of various modern adjuvants in vaccine formulations is extensive. Many studies have demonstrated a potent immune response upon immunization with various recombinant products and modern adjuvant formulations using animal models (Reviewed in Vogel, 1998; O'Hagan 1998; Cox and Coulter, 1997; Gupta and Siber, 1995; Hughes and Babiuk, 1994). A few of the formulations appear superior in terms of efficacy and safety and are currently being tested in human clinical trials. However, the efficacy of any given adjuvant is immunogen dependent and thus predicting which combinations will be successful cannot be done reliably.

Among the most efficacious of the modern formulations are iscoms and iscom matrix (U.S. Pat. No. 5,679,354) which have demonstrated efficacy with influenza, respiratory syncytial virus, leishmaniasis, malaria, and HIV immunogens in animals (Andersson et al., 1999; Verschoor et al. 1999; Hu et al., 1998; Deliyannis et al., 1998; Papadopoulou et al., 1998; Bengtsson and Sjolander, 1996; Barr and Mitchell, 1996; Jones et al., 1995; Ronnberg et al., 1995; Takahashi et al., 1990). The Ribi adjuvant system, comprised of the detoxified endotoxin derivative, monophosphoryl lipid A, trehalose dicorynomycolate, with or without cell wall skeleton in a metabolizable oil, has also been demonstrated to induce potent immune responses in animal studies (Baldridge and Ward, 1997; Todd et al., 1997; Lipman et al., 1992; Johnson and Tomai, 1990; Kenney et al., 1989; Tomai and Johnson, 1989; Ribi et al., 1984). While these adjuvants have been shown to be effective with certain immunogens, there are also reports describing less than desirable effectiveness including non-protective responses with both iscom matrix (Echinococcus granulosus tegumental antigens—Carol and Nieto, 1998; herpes simplex virus glycoprotein—Simms et al., 1998; Leishmania major Parasite Surface Antigen—Sjolander et al., 1998) and Ribi adjuvant system (synthetic polypeptide—Deeb et al., 1992; Pasteurella multocida antigen—McClimon et al., 1994; trinitrophenol-hen egg albumin—Bennet et al., 1992; Smith et al., 1992). Thus, while the potential efficacy of a number of adjuvants are described in the literature, the optimal adjuvant for any given immunogen and any given disease target must be determined empirically.

We have demonstrated that the combination of certain modern adjuvants, in particular iscom matrix and the Ribi adjuvant system (RAS), with our Drosophila-expressed prM80%E flavivirus subunits results in an exceptionally potent vaccine formulation. iscom matrix is an immunomodulating agent that has an iscom-like structure and comprises within the iscom-like structure at least one lipid and at least one saponin, and a pharmaceutically acceptable vehicle, which sold under the trade name "ISCOMATRIX. This combination induces very high titer virus neutralizing antibodies in mice and monkeys and affords significant protection from viral challenge. However, combination of our recombinant prM80%E with other modern adjuvants failed to induce this potent immune response suggesting the uniqueness of the combination. Thus, the unique combination of flavivirus prM80%E expression constructs and the Drosophila expression system has allowed us to overcome the major limitations previously encountered in efforts to efficiently produce recombinant flavivirus subunit proteins. The addition of specific modern adjuvants to the recombinant product is effective in overcoming the final hurdle to production of an efficacious flaviviral recombinant subunit vaccine by significantly boosting the immune response in vaccinated animals. Examples illustrating the efficacy of the unique combination are contained herein below.

DISCLOSURE OF THE INVENTION

The invention provides vaccines containing, as an active ingredient, a Drosophila cell-secreted, recombinantly-produced form of truncated flavivirus envelope glycoproteins. The invention also includes a modern adjuvant as a critical component of the effective vaccine formulation The vaccines are capable of eliciting the production of neutralizing antibodies against flaviviruses and protecting against challenge with live virus. In the illustrations below, all products are expressed as a polyprotein including prM, and the mature recombinant 80%E products are secreted from *Drosophila melanogaster* Schneider 2 cells using the human tissue plasminogen activator secretion signal sequence (tPAL).

Thus, in one aspect, the invention is directed to a vaccine for protection of a subject against infection by a flavivirus. The vaccine contains, as active ingredient, the truncated envelope protein of a flavivirus and a modern adjuvant to modulate the immune response to the envelope protein. The truncated E is secreted as a recombinantly produced protein from insect cells. The vaccine may further contain additional truncated flavivirus E proteins similarly produced.

MODES OF CARRYING OUT THE INVENTION

Figure 1:
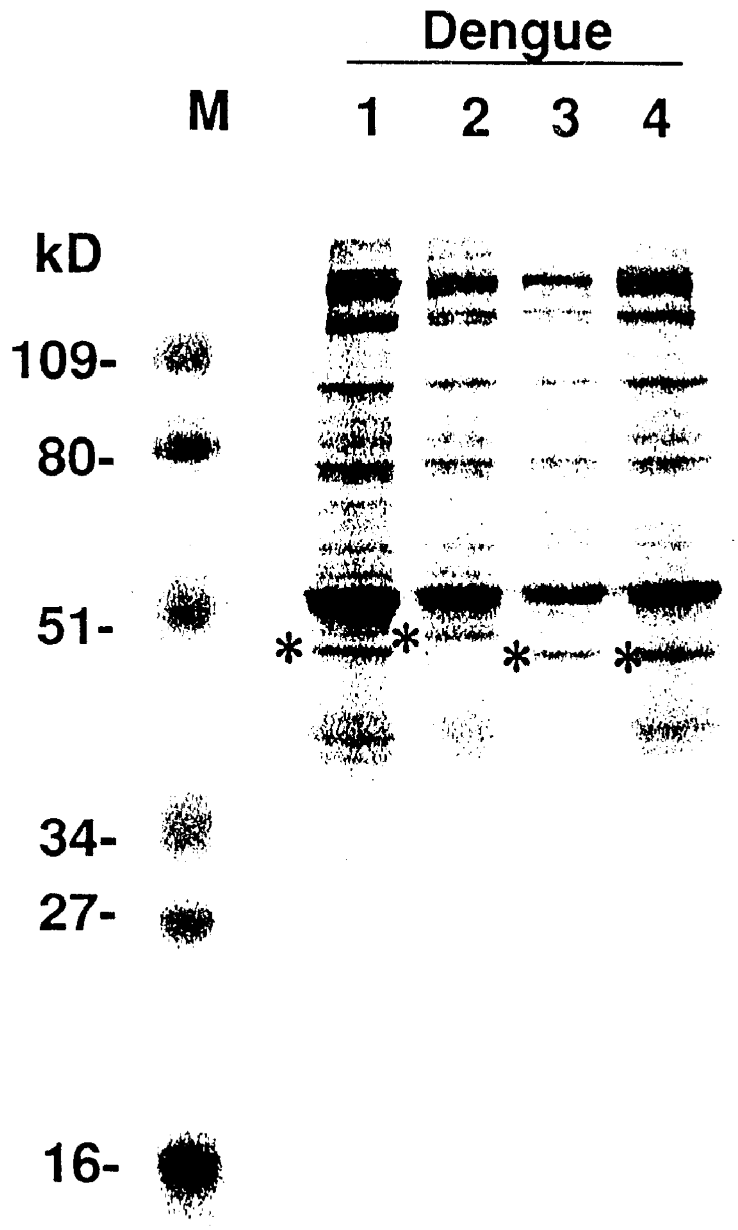
FIG. 1 shows SDS-PAGE analysis of crude media from S2 cells transfected with DEN-1, -2, -3, and 4 prM80%E expression constructs.

The invention provides, for the first time, a subunit flavivirus vaccine with increased immunogenicity that can be efficiently produced and secreted using a recombinant expression system and that is effective in inducing a strong virus neutralizing response to flaviviruses. Although many attempts have been made to obtain such a subunit vaccine, previous studies have not approached the quantitative or qualitative levels of antigen expression required to meet the requirements for a commercial vaccine product. The present applicants have found that recombinantly-engineered carboxy-terminally truncated flavivirus envelope glycoproteins, corresponding to amino acids 1–395, are efficiently secreted by a certain convenient eukaryotic recombinant host, in a form that permits processing to mimic the native conformation of the protein. The efficient secretion of the proteins into the culture medium facilitates purification. Furthermore, the secreted forms are able, especially when administered in the presence of certain modern adjuvants, to raise high titer virus neutralizing antibodies in animals and to protect these animals from challenge with live virus. Thus, these proteins represent a useful component of a vaccine for protecting subjects against flavivirus infection.

As used herein, "80%E" refers to a polypeptide that spans from Met 1 to Gly 395 of the DEN-2 envelope protein. The sequences described in the present application represent the envelope protein from dengue type 2 virus; three additional distinct dengue serotypes have been recognized. Therefore, "80%E" also refers to the corresponding peptide region of the envelope protein of these serotypes, and to any naturally occurring variants. "80%E" also refers to the corresponding peptide region of the envelope protein of other flaviviruses including but not restricted to Japanese encephalitis, Yellow Fever, Tick-borne encephalitis and hepatitis C viruses. All of the 80%E proteins are produced from vectors containing the DNA encoding the flavivirus prM as a fusion with 80%E. The fusion protein is processed by cellular enzymes to release the mature 80%E proteins.

Recombinant techniques provide the most practical approach for large-scale production of these subunits for vaccine purposes. However, to be efficacious these proteins must undergo correct processing and assume a conformation similar to that of native dengue envelope protein. In order to achieve this, the recombinant production must be conducted in eukaryotic cells, preferably *Drosophila melanogaster* cells, as efficient production of the correctly processed and properly folded product must be achieved in order to make a cost-effective vaccine feasible.

As previously described, it has been found that efficient secretion of biologically active mature truncated flaviviral envelope protein is best achieved using the *Drosophila melanogaster* Schneider-2 cell line. The expression of the products is driven by an efficient insect cell promoter (Drosophila metallothionein promoter) and secretion is targeted using a eukaryotic secretion leader (human tissue plasminogen activator secretion leader) as well as the flavivirus prM protein which contains the secretion signal for E. Other promoters and secretion leaders can also be used. In general, the invention includes expression systems that are operable in eukaryotic cells and which result in the efficient secretion of truncated flavivirus envelope proteins into the medium. Thus, useful in the invention are cells and cell cultures which contain expression systems resulting in the production and secretion of mature truncated flavivirus envelope proteins.

The properly processed truncated E proteins are recovered from the cell culture medium, purified, and formulated into vaccines. Purification employs standard techniques and is a matter of routine optimization. Suitable formulations, which will include an adjuvant, must be determined empirically.

The active vaccines of the invention can be used alone or in combination with other active vaccines such as those containing attenuated or killed forms of the virus, or those containing other active subunits to the extent that they become available. The vaccines may contain only one subunit as an active ingredient, or additional isolated active components may be added. Corresponding or different subunits from one or several serotypes may be included in a particular formulation.

To immunize subjects against dengue fever, for example, the vaccines containing the subunit are administered to the subject in conventional immunization protocols involving, usually, multiple administrations of the vaccine. Administration is typically by injection, typically intramuscular or subcutaneous injection; however, other systemic modes of administration may also be employed. Although the technology is not as well developed, transmucosal and transdermal formulations are included within the scope of the invention as are effective means of oral administration.

In the examples below, the expression, secretion, processing, and immunogenicity of the secreted flavivirus glycoproteins are demonstrated. The products are recombinantly produced as modified prM-80%E fusions that are efficiently processed by host cell proteases to remove the prM portion and secreted from Drosophila cells. The secreted 80%E products are secreted at high levels, up to 50 μg/ml. Furthermore, based upon reactivity with conformationally sensitive monoclonal antibodies, the secreted 80%E products have native-like conformation and immunization of mice and/or non-human primates with 80%E, induces a potent virus-neutralizing immune response.

The following examples are intended to illustrate but not to limit the invention.

EXAMPLE 1

Isolation of Dengue Viral RNA

Cell pellets infected with dengue virus type 1, 3, or 4 were blind passaged in C6/36 cells. The entire culture, cells and medium, was harvested and titered on Vero cells. Monolayer cultures of C6/36 cells were infected at an MOI of 0.1 pfu/cell and the cells and the medium harvested separately 4, 5, and 6 days post infection. Virus was pelleted from the clarified medium by centrifugation at 150,000×g for 3 hours. Both the virus infected cells and pelleted virus were lysed in acid guanidine thiocyanate, and the RNA purified by phenol-chloroform and chloroform extraction followed by alcohol precipitation. Viral RNA from DEN-1 strain 258848, DEN-3 strain CH53489, and DEN-4 strain H241 were also prepared according to this method.

EXAMPLE 2

Preparation of Dengue 2 prM80%E (Envelope) cDNA Expression Clone

A cDNA clone derived from dengue serotype 2 (DEN-2) strain PRI 59/S1 (Eckels et al., 1980, Infect. Immun. 27:175–180) was used as the starting material for the generation of all DEN-2 expression plasmids. The cDNA clone pC8 (Hahn et al., 1988. Virology 162:167–180) was used as template for the amplification of the portion of the genome that encodes the amino terminal 80% of the envelope protein (80%E). This amplification was accomplished using the Polymerase Chain Reaction (PCR) with primers D2E937p and D2E2121m. In this notation for the primers, the virus serotype is first indicated (D2 for DEN-2), then the corresponding Dengue gene, i.e., in this case envelope, E, is noted. The number indicates the location of the primer in the cloned sequences using the numbering of Hahn et al. (1988), and finally the notation shows whether the oligonucleotide primes the plus (p) or the minus (m) strand synthesis. The sequence in the primers corresponding to dengue cDNA are written in uppercase letters, nondengue sequence is written in lowercase letters.

```
D2E937p2

        BglII                                              (SEQ ID NO:1)
5'-cttctagatctcgagtacccgggacc ATG CGC TGC ATA GGA ATA TC-3'
     XbaI  XhoI   SmaI

D2E2121m

          SalI                                             (SEQ ID NO:2)
5'-gctctagagtcga cta tta TCC TTT CTT GAA CCA G-3'
     Xba I       End End
```

The D2E2121m primer placed two stop codons after the 395th codon of E. The 80%E amplified cDNA fragment was digested at the Xba I sites in the cloning adapters and cloned into the Nhe I site of pBR322 to obtain p29D280E. The nucleic acid sequence of the cloned 80%E was determined using chain termination sequencing. This analysis identified a single silent PCR-introduced mutation at nucleotide 2001 (AAC/Asn to AAT/Asn).

A cDNA clone of DEN-2 PR 159/S1 designed to encode the preMembrane, Membrane, and Envelope genes (prM100%E) was constructed by PCR amplification essentially as described above for the subcloning of 80%E. This cDNA clone includes nucleotides 439 to 2421 of the DEN-2 genome (numbering of Hahn et al., pC8). The dengue cDNA fragment was generated using synthetic oligonucleotide primers D2pM439p and D2E2421m and plasmid pC8 (Hahn et al, 1988,) as template. In addition to DEN-2 specific sequences, the primers contained the identical adaptor sequences described above except that a methionine codon (ATG) was included immediately preceding the first codon of the preMembrane sequence (phenylalanine). The primers are:

```
D2prM439p

        BglII                                                (SEQ ID NO:3)
5'-attctagatctcgagtacccgggacc atg TTT CAT CTG ACC ACA CGC-3'
     XbaI  XhoI  SmaI

D2E2421m

          SalI                                               (SEQ ID NO:4)
5'tctctagagtcga cta tta GGC CTG CAC CAT AAC TCC-3'
     XbaI      END END
```

The PCR-generated prM100%E cDNA fragment was digested with the restriction endonuclease Xba I and ligated into the Xba I site of pBluescript $SK^+$ (Stratagene, San Diego, Calif.) to obtain the plasmid p29prME13. DNA sequence analysis of the PCR-generated cDNA clone identified three PCR-introduced nucleotide differences between pC8 and p29prME13. A T→C transition at nucleotide 1255 resulted in a silent mutation. The A→G transition at nucleotide 1117 resulted in the conservative amino acid substitution of a valine for an isoleucine. The final transition observed at nucleotide 1750 replaced a methionine with a valine.

To generate a cDNA subclone representing prM80%E, a 794 bp Bam HI-Sal I fragment from p29prME13 encoding the carboxy terminal end of envelope was removed. This fragment was replaced with a 431 basepair Bam HI-Sal I fragment from p29D280E that encodes the carboxy terminus of the truncated envelope glycoprotein, 80%E. The Bam HI site is a naturally occurring site within the envelope cDNA, and the Sal I site is an engineered site that immediately follows the stop codons encoded by the PCR primers. The resulting truncated cDNA clone, p48BSprM80E, was confirmed by restriction digestion and DNA sequence analysis to encode the entire prM protein and amino acids 1 through 395 of the envelope glycoprotein. This cDNA clone maintains the transition at nucleotide 1117 (isoleucine to valine amino acid change), maintains the silent mutations at nucleotides 1255 and 2001, but repairs the transition at nucleotide 1750.

The expression vector constructed to secrete DEN2 80%E from *Drosophila melanogaster* S2 cells was based on the pMttbns vector (Culp et al., 1991). The vector pMttbns is pBR322 based and contains a Drosophila metallothionein gene promoter ($P_{Mtn}$), the human tissue plasminogen activator leader sequence ($tPA_L$), and the SV40 early polyadenylation signal (Culp et al., 1991). A 15 bp Bam HI DNA fragment containing an Xho I site was deleted from pMttbns to make pMttΔXho, in which the Bgl II and Xho I restriction endonuclease sites are unique. This change was confirmed by sequence analysis. A Bgl II-Sal I fragment encoding full-length DEN2 prM and amino acids 1–395 of envelope was obtained by restriction digestion of plasmid p48BSprM80E and ligated into pMttΔXho digested with Bgl II and Xho I. This construction resulted in the prM80%E fragment being fused to the $tPA_L$ sequence. During normal maturation of tissue plasminogen activator the 20 amino acid pre-peptide region of the leader sequence is removed by signalase in the endoplasmic reticulum and the 11 amino acid pro-peptide region is enzymatically removed in the Golgi. The resulting plasmid, pMttD2prM80%E, was confirmed by restriction digestion and limited sequence analysis. The nucleotide and predicted amino acid sequences (SEQ ID NO:5 and SEQ ID NO:6, respectively) of the $tPA_L$-prM80E fusion gene are shown below:

```
ATG          GGAGCCAGATCTCGAGTACCCGGGACCATGTTT . . . . GGA     TAA
Met-20aa-11aa-GlyAlaArgSerArgValProGlyThrMetPhe1 . . . Gly395 END
   Pre Pro-tPA       Linker Sequence         DEN-2 prM80%E
```

The tPA pre- and propeptide regions are delineated by pre and pro-tPA, respectively, and the dengue sequences are indicated in bold type. The $Phe_1$ residue is the N-terminal amino acid of the prM protein and $Gly_{395}$ is residue 395 from the amino terminal end of the envelope glycoprotein. The linker sequence includes restriction sites for introducing foreign gene sequences.

Given the possibility of adverse effects due to the mutation at nucleotide 1117 (valine instead of isoleucine at amino acid 61 of envelope) the mutation was corrected in the pMttD2prM80%E expression clone. We identified a unique restriction endonuclease fragment encompassing mutation 1117 that enabled us to replace the fragment in pMttD2prM80%E with the corresponding fragment from pC8 in a single step. Thus, a 783 bp Afl II fragment (nucleotides 1101–1783) was removed from pMttD2prM80E, and the corresponding Afl II fragment from pC8 was ligated in its place. The resulting plasmid, pMttD2prM80E($Ile_{61}$).4, possesses a single silent mutation at 2001 and produces an 80%E polypeptide equivalent to the wild type viral E protein sequence. The features and sequence of the expression plasmid are listed in Appendix 1. Because the software used for the analysis limits file names to eight characters, the plasmid name listed in Appendix 1 is listed as MttprM80.

EXAMPLE 3

Cloning of prM80%E from DEN-1 (strain 258848), DEN-3 (strain CH53489) and DEN-4 (strain H241)

DEN-1, -3, and -4 prM80%E cDNA constructs analogous to the DEN-2 prM80%E construct were cloned and expressed in Drosophila Schneider 2 cells. The cloning strategy used to prepare the prM80%E cDNA utilized the reverse transcriptase-polymerase chain reaction (RT-PCR) procedure. Briefly, total RNA was prepared from infected C6/36 mosquito cell pellets, as described in Example 1. RT-PCR reactions utilized dengue-specific synthetic oligonucleotide primers to amplify the desired fragment The cDNA fragment generated for DEN-1 encompasses nucleotides 422 to 2102 on the genomic map (consensus map of DEN-1 strains); for DEN-3, nucleotides 437 to 2113 on the genomic map (based on the reference strain D3H87); and for DEN-4, the selected fragment encompasses nucleotides 441 to 2120 on the genomic map (strain H241). The PCR products for DEN-1 and -4 were digested with the restriction endonucleases BglII and XhoI (sites contained in the oligonucleotide primers) and cloned directly into the Drosophila expression plasmid pMttΔXho digested with BglII and XhoI (see example 2). The PCR product for DEN-3 was digested with BglII and SalI and cloned directly into the Drosophila expression plasmid pMttΔXho digested with BglII and XhoI. Clones from each of the three dengue serotypes (DEN-1, -3, and -4) were selected for DNA sequence analysis.

Sequence analysis of a molecular clone of DEN-1 prM80%E (clone #2) derived from strain 258848 demonstrated that it has a single PCR-induced error that resulted in an amino acid substitution. Four other clones that had been cryopreserved, but were not sequenced initially, were then sequenced. Clone #7 was found to possess a corresponding restriction fragment (BglII-XbaI) free of PCR errors, and was subsequently used to correct the error by fragment substitution in clone #2. The DNA sequence of the resulting clone, pMttD1prM80Ef.6 was verified by sequence analysis and this clone was used for all subsequent expression work.

Sequence analysis of molecular clones of DEN-3 prM80%E derived from strain CH53489 demonstrated that one clone, pMttD3prM80E.11, contained native DEN-3 sequence. This clone was used for all subsequent expression work.

Sequence analysis of two selected molecular clones of DEN-4 prM80%E derived from strain H241 indicated that each of the clones contained a single PCR-induced error that resulted in an amino acid substitution. Clone #2 was selected for repair because it showed the highest expression levels in Drosophila Schneider cells. Four other clones that had been cryopreserved, but were not sequenced initially, were then sequenced. Clone #4 was found to possess a corresponding restriction fragment free of PCR errors, and was used to correct the error by fragment substitution in clone #2. The sequence of the resulting clone pMttD4prM80Ef.3 was verified by DNA sequence analysis.

Extensive comparison of the pMttD4prM80Ef.3 sequence with various published sequences indicated sequence heterogeneity around a predicted glycosylation site at amino acid 153 of E. While the original report of DEN-4 H241 sequence suggested that the glycosylation site is intact (Kawano et al., 1993), subsequent reports, both published (Lanciotti et al., 1997) and unpublished, suggested that in certain strains, including some H241 isolates, this glycosylation site is not maintained due to an amino acid change from a threonine to an isoleucine. Our clone encoded an isoleucine at this position and thus would not contain the glycosylation site. As this lack of glycosylation could adversely affect the expression or immunogenicity of the product we conducted site directed mutagenesis to change the isoleucine at amino acid 155 of E to a threonine. Using standard techniques for oligonucleotide directed mutagenesis we mutated the codon from ATA to ACA to encode a threonine. The resultant clone, pMttprM80Ef.3+G.13, was confirmed by sequence analysis and used for all subsequent expression studies.

EXAMPLE 4

Construction of cDNA Expression Clone for JEV prM80%E

A JEV construct analogous to those described above for the dengue viruses was constructed and expressed in Drosophila S2 cells. The sequence encoding the prM and 80%E protein products of JEV was PCR amplified from a cDNA clone, 1079.14, containing nucleotides 1 through 5576 of JEV strain JaOArS982 (Sumiyoshi et al., 1992). Oligonucleotide primers JEpM477p and JEE2177m were designed to amplify the fragment corresponding to nucleotides 477–2177 of JEV encoding prM and 80%E. The 5' end primer contained a BglII site while the 3' end primer contained a XhoI site to facilitate cloning. The PCR product was digested with these enzymes and cloned directly into the pMttΔXho vector previously digested with the same restriction endonucleases. The identity of the resultant expression clones was confirmed by restriction digestion and limited sequence analysis.

EXAMPLE 5

Transfection of Drosophila Cells with Expression Plasmids

The Drosophila expression system is based on the cotransfection of S2 cells with the expression plasmid containing the gene of interest and a selection plasmid. The plasmids cointegrate at high copy number into the genome and selection for presence of the selection plasmid also favors cells which contain the integrated expression construct The selection plasmid used in the generation of our cell lines, pCoHygro (Van der Straten et al., 1987; Van der Straten et al., 1989), carries the *E. coli* hygromycin B phosphotransferase gene under the transcriptional control of a *D. melanogaster copia* transposable element long terminal repeat and confers resistance to hygromycin B.

S2 cells were plated at $1\times10^6$ cells/ml in 4 ml of Schneiders medium (Gibco-BRL) containing 10% heat inactivated fetal bovine serum (FBS; Hyclone) in 60 mm tissue culture dishes the day prior to transfection. The cells were transfected using the calcium phosphate coprecipitation method (Wigler et al., 1977). Briefly, 20 $\mu$g of expression plasmid, (e.g. pMttD2prM80E($I1e_{61}$).4 and 1 $\mu$g of selection plasmid, pCoHygro, were combined with a calcium solution. This mixture was slowly added to an equal volume of HEPES buffered saline containing phosphate to give a fine calcium phosphate—DNA precipitate. The precipitate was plated onto the S2 cells and incubated overnight After approximately 16 hours the transfected cells were washed with two changes of medium and replated in 5 ml fresh Schneiders medium containing 10% FBS. Three days later hygromycin B (Boehringer Mannheim Biochemicals) was added to a final concentration of 300 $\mu$g/ml. Following transfection the cells were maintained in selective media containing 300 $\mu$g/ml hygromycin B. All cells were maintained at 26° C. in a humidified chamber. Expression of recombinant products was evaluated by plating the cells at $2\times10^6$ cell/ml in serum-free medium (Excell 400, JRH Biosciences) and inducing the promoter with the addition of copper sulfate at 0.2 mM final concentration. The cells and culture supernatants were harvested day 7 post-induction and evaluated by SDS-PAGE and Western blot.

EXAMPLE 6

Characterization of the Secreted Flavivirus 80%E Products

Analysis of intracellular and secreted proteins by SDS-PAGE and Western blot revealed that the recombinant 80%E products (DEN-1, -2, -3, -4, and JEV) are efficiently produced and secreted into the medium. A ~48 kilodalton (kD) band is visible by Coomassie blue staining in unconcentrated medium and is recognized by serotype-specific polyclonal antisera (hyperimmune mouse ascitic fluid—HMAF). Comparisons of intracellular to secreted proteins demonstrated that the products are efficiently secreted. A time course revealed that the 80%E proteins accumulate in the medium over time. Estimates of secretion level based on Coomassie stained gels range from 5–20 mg/l in uncloned cell populations at day 7 post-induction as shown in FIG. 1.

Specifically, FIG. 1 shows a SDS-PAGE analysis of crude media from S2 cells transfected with DEN-1, DEN-2, DEN-3, and DEN-4 80%E. 10 $\mu$l of crude media was loaded on non-reducing 12% SDS-PAGE gels and stained with Coomassie Blue. The location of the 80%E bands are indicated by an arrow. Note under these conditions that DEN-2 80%E migrates slightly slower than the DEN-1, -3, and -4 80%E bands.

Sensitivity of the secreted 80%E to endoglycosidases was evaluated by molecular weight shift of the protein in SDS-PAGE and Western immunoblots following endoglycosidase treatment. Resistance of the secreted 80%E to Endoglycosidase Hf (Endo Hf; New England Biolabs) and sensitivity to Peptide:N-glycosidase F (PNGase F; New England Biolabs) digestion indicated that the secreted product contains N-linked glycosylation, and suggest a mannose-3 type glycosylation, typical of insect cell expression systems (data not shown).

Immunofluorescence studies demonstrated that between 5–25% of cells in an uncloned population are antigen positive and that the antigen positive cells are recognized by a range of conformationally sensitive and insensitive anti-flavivirus MAbs. The panel of MAbs encompasses a range of epitope specificities, including those that are dengue type specific, dengue complex or subcomplex specific, and flavivirus group specific. Table 1 summarizes the spectrum of 80%E binding activity of selected MAbs. Reactivity of the MAbs with S2 cell-expressed DEN-2 prM80%E is consistent with the expected profile. Each of the MAbs known to bind DEN-2 E protein (4G2, 5A2, and 9D12; Henchal et al., 1982; Megret et al., 1992) were shown to bind the subunit antigen. As expected, MAb 2H2 (specific to dengue prM/M protein) was positive by IFA assay of S2 DEN-2 prM80%E cells, since the M protein is also expressed with the prM80%E construct MAb 7E 11, specific to dengue NS1 protein, was not reactive by IFA, consistent with the absence NS1 sequences in the prM80%E construct.

TABLE 1

Indirect Immunofluorescence Staining of DEN-2 prM 8O% E Transfected S2 Cells

| MAb | Specificity | IFA* |
|---|---|---|
| 2H2 | prM/M Dengue Complex | ++ |
| 4G2 | E Flavivirus group | +++ |
| 5A2 | Domain B of E Dengue Complex (linear epitope) | + |
| 7E11 | NS1 Dengue 2 | – |
| 9D12 | Domain B of E DEN 1–3 subcomplex | +++ |

*Indirect immunofluorescence analysis of permeabilized (prM) 80% E transformed Drosophila cells.
Subjective index of staining intensity:
– = negative;
+ = positive;
+++ = strongly positive.

EXAMPLE 7

Cloning of Transfected S2 Cells by Limiting Dilution Using Removable Feeder Layers Immunofluorescence studies demonstrated that from 5–25% of cells were positive for flavivirus 80%E antigen expression (Example 6), therefore if the antigen positive cells could be cloned from this mixed population, then expression levels would likely increase. Methods to clone the cells were developed with the goal of achieving a clonally pure, high-level expressing cell line. As the S2 cells are very sensitive to low cell density significant optimization was required.

Subcloning of the cells was accomplished using a removable feeder layer to allow the cells to survive the subcloning process. Cells were plated at specific cell densities in complete IPL-41 medium containing 10% FBS and 150 μg/ml hygromycin B. We have found that serum is required for the cells to survive subcloning and that the concentration of hygromycin B must be reduced to 150 μg/ml to avoid precipitation of hygromycin B crystals in the 96 well dishes. First round subcloning was conducted at 30 cells/well in 96 well dishes. The inserts which support the removable feeder layer are 0.2 μm Anopore membrane tissue culture inserts (Nunc). Feeder layers which consisted of homologous cells were plated at 1000 cells/insert. Feeder layers were removed once they reached confluence, usually in one to two weeks. Once significant outgrowth of the subclones was achieved, they were expanded first in 96 well, then 6 well, and finally 60 mm tissue culture dishes into serum-free medium. Expression was initially evaluated by induction of subclones in separate 96 well dishes and dot blot analysis. The best expressors were then expanded and evaluated in side-by-side inductions by SDS-PAGE and Western blot analysis as described above (Example 6). The second and third rounds of subcloning was conducted essentially as described above except that the cells were plated at 1 cell/well instead of 30 cells/well and the number of cells in the insert was increased to 10,000.

Using this method we have generated a clonally pure DEN-2 80%E cell line which expresses 80%E at 25–35 mg/l. Cells expressing DEN-1, DEN-3, and DEN-4 80%E have been through the first round of subcloning and expression levels of 20–50 mg/l have been achieved.

EXAMPLE 8

Large-scale Culture of Transformed Drosophila S2 Cell Lines

Efforts to scale-up cultures of transformed Drosophila S2 cells have employed a New Brunswick Scientific (NBS) Bioflo 3000 bioreactor with a 5 liter vessel. This instrument is a stirred tank system employing a marine blade impeller. A significant consideration in the development of these methods is the cost of the culture medium used. In stationary culture, we have used Schneider (Gibco-BRL) and Excell 400 (JRH Biosciences) media for the growth of Drosophila cells. When fully supplemented, these media are relatively costly. Therefore, we sought a suitable medium that is less costly. Based on a report by Olsen et al. (1992), IPL-41 medium (Gibco-BRL) supports the vigorous growth of Drosophila cells at a cost of ~$10 per liter. Based on a large number of runs we have developed conditions which facilitate effective production runs. The conditions are summarized below:

Standardized Bioreactor Conditions

- Medium: IPL-41 (powdered; Gibco-BRL)
- Deionized water
- Medium supplements (final concentrations in medium are listed):
  - Yeastolate, 3.33 g/l (Gibco-BRL)
  - Lipid concentrate, 1% (v/v) (Gibco-BRL)
  - Pluronic polyol F-68, 0.1% (w/v)(Gibco-BRL)
- Dissolved oxygen: maintained at 50% air saturation
- Gas sparging rate: 0.133 liter gas/liter medium/minute, using a ring sparger
- Agitation rate: 80 rpm using two marine blades
- pH: 6.4, maintained by acid-base feed
- Culture volume: 3–4 liters
- Schneider cell inoculation density: $1\times10^6$ cells/ml
- Cell density at induction with 0.2 mM $CuSO_4$:2–$3\times10^6$ cells/ml
- Cell density at harvest: $\geqq 1\times10^7$ cells/ml A growth curve and corresponding Western blot of the time-course of 80%E secretion into medium during a typical bioreactor run is shown in FIG. 2.

Figure 2A:
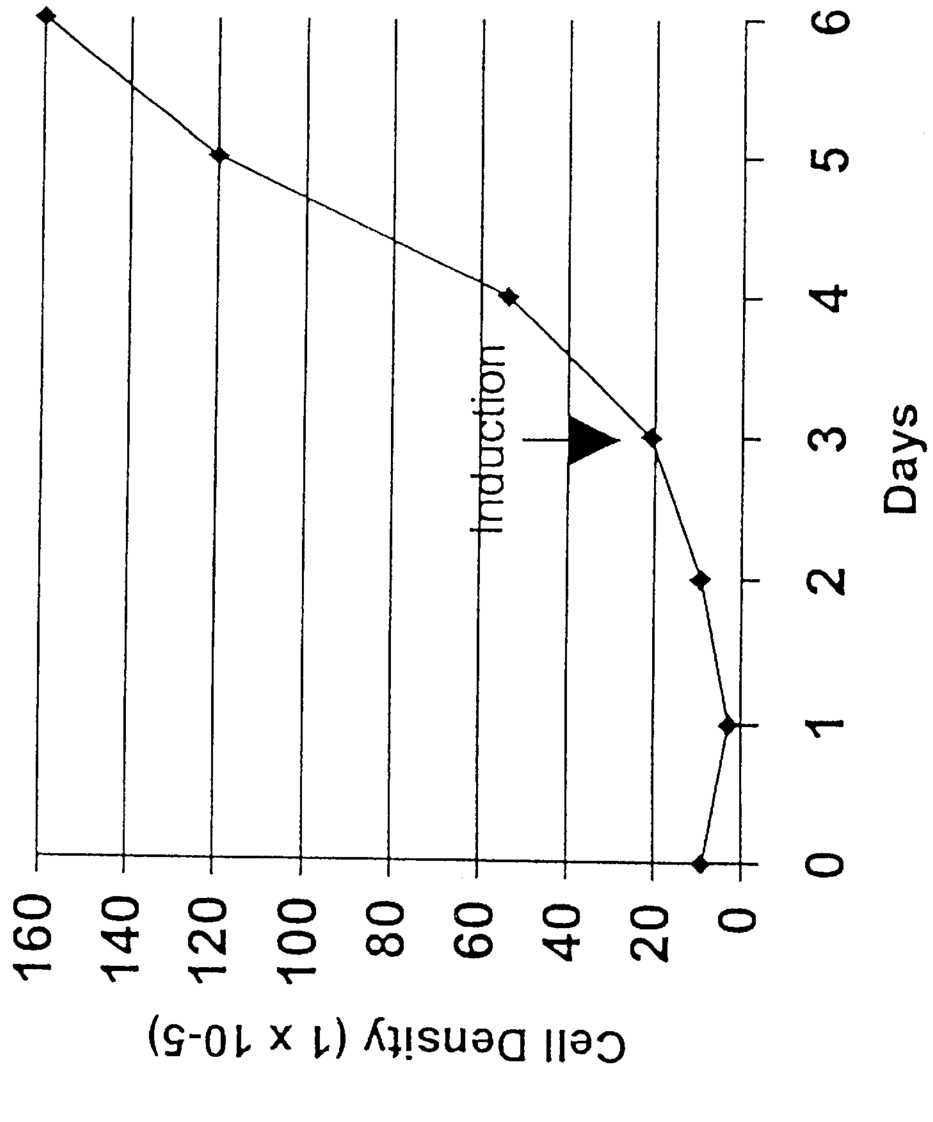
FIGS. 2*a* and 2*b* presents a typical growth curve for transfected S2 cells in the bioreactor and Western blot analysis of DEN-2 80%E expression.
Figure 2B:
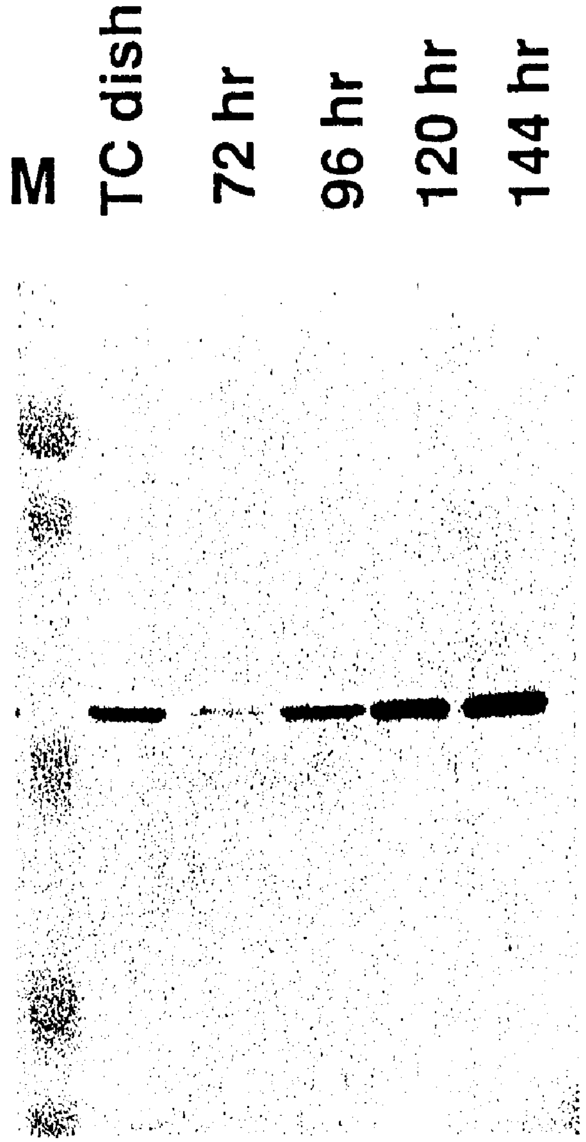

In this Figure, the growth curve of S2 DEN-2 prM80%E cells cultured in a bioreactor is shown in FIG. 2*a* and the Western blot analysis of secreted DEN-2 80%E taken from the same culture at the indicated time points is shown in FIG. 2*b*. The medium was harvested from a tissue culture dish ("TC dish") 7 days post-induction.

EXAMPLE 9

Immunoaffinity Purification of Flaviviral Antigens

The significant expression of various flavivirus recombinant 80%E subunits in S2 cells, coupled with the need to test purified antigens in mice necessitated development of rapid purification methods. Initially, we used immunoaffinity chromatography (IAC) to purify the antigens for testing in mice.

Immunoaffinity chromatography relies on the selective, high-affinity recognition of, and reversible interaction between, an antibody and an antigen. For flavivirus antigen purification, two conformationally sensitive monoclonal antibodies (MAb), 9D12 (DEN-1, -2, -3) and 4G2 (DEN-4, JEV), were chosen. The antibodies were coupled to N-hydroxysuccinimide (NHS)-activated Sepharose columns (HiTrap, Pharmacia) by loading the columns with antibody that had been buffer-exchanged into 0.1 M $NaHCO_3$, 0.5 M NaCl (pH 8.3) and incubating at room temperature for three hours. Uncoupled antibody was flushed from the column and any remaining NHS sites were deactivated by perfusing the column with 0.5 M ethanolamine.

In preparation for chromatography, the cell-free culture medium was brought to 0.05% (w/v) sodium azide (using a 10% stock) and passed through a 0.2 μm filter (Serum Acrodisc®, Gelman Sciences). Culture medium volume corresponding to roughly 1 mg of 80%E was loaded onto the IAC column pre-equilibrated with phosphate-buffer saline (PBS: 140 mM NaCl, 3 mM $NaH_2PO_4$ and 8 mM $Na_2HPO_4$, pH 7.2) containing 0.05% sodium azide. Unbound material was flushed from the column by washing with PBS (containing 0.05% sodium azide) until optical density (measured at 280 nm) of the wash reached baseline. 80%E elution was achieved using 100 mM glycine pH 2.5 with in-line monitoring of optical density at 280 nm to ensure accurate collection of the protein peak. Flow-rate for the loading and PBS wash steps was ~0.6 ml/min, but the low pH elution was done at 1.5–2 ml/min. Acid-eluted material was immediately neutralized with roughly $1/10^{th}$ volume of 1 M Tris pH 8, then buffer-exchanged into PBS using a Centricon-30 (Amicon), and sterile-filtered through a 0.2 μm membrane (Acrodisc 13®, Gelman Sciences).

Figure 3:
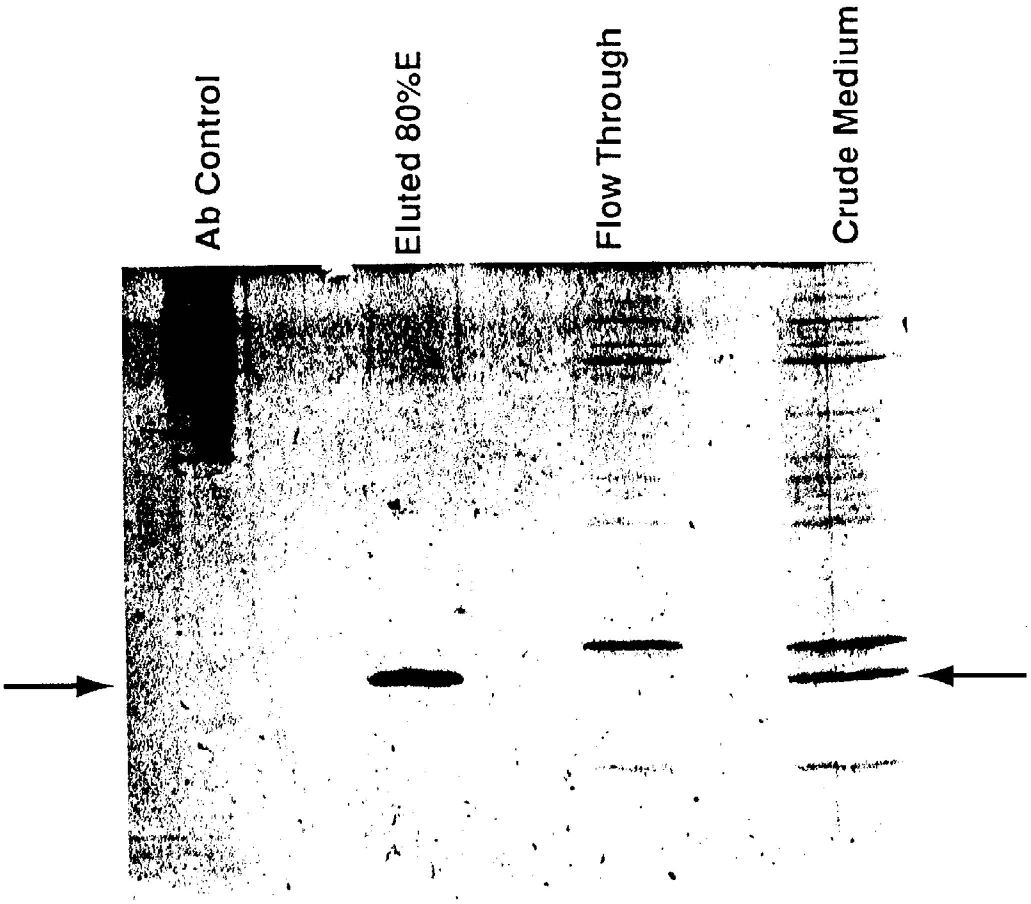
FIG. 3 shows a silver-stained SDS-PAGE analysis of fractions from the dengue immunoaffinity column.

Analysis of unpurified starting medium, flow-through and eluted antigen-containing fractions by SDS-PAGE indicated typical product yields to be roughly 80%, with about 5% of the starting 80%E being lost in the flow-through fraction. Final product purity is generally about 80–90%. SDS-PAGE analysis of a typical purification run is shown in FIG. 3. Specifically, this figure shows a silver stained SDS-PAGE gel of fractions from a flavivirus immunoaffinity chromatography column. A portion of each fraction was diluted 1:1 with SDS loading buffer with no reducing agents, and loaded onto a 12% polyacrylamide gel. The resolved proteins were visualized by silver staining. Arrows indicate the position of dengue 80%E. The antibody control lane contains 5 $\mu$g of antibody as a standard.

EXAMPLE 10

Purification by Hydroxyapatite/size-exclusion High Performance Liquid Chromatography (HTP-SEC)

Drosophila Schneider 2 cell culture media containing recombinant DEN 80%E antigens (serotypes 1–4) are diafiltered against the hydroxyapatite (HTP; BioRad) column buffer (10 mM sodium phosphate, pH 6.45) using a tangental flow apparatus equipped with 30 kDa molecular weight cut-off membranes. The buffer-exchanged media are then applied to an HTP column and eluted with a step-gradient of 50, 100, 150, 200 and 400 mM sodium phosphate buffers, pH 6.45. Product elution is monitored by UV spectroscopy (absorbance at 280 nm) and SDS-PAGE analysis to identify fractions containing 80%E. The fractions containing 80%E are concentrated by ultrafiltration and further purified by HPLC-SEC using a TSK G3000SWXL column (TosoHaas) and a mobile phase of 20 mM sodium phosphate, pH 6.45, containing 100 mM NaCl. Product elution is monitored by UV spectroscopy ($A_{280}$). Each of the four serotype DEN 80%E antigens can be purified to greater than 95% homogeneity in yields of greater than 60% by this method.

EXAMPLE 11

Evaluation of Immunogenicity of Purified DEN-2 80%E in Mice Using Several Different Adjuvants Adult mice were immunized with DEN-2 80%E in a variety of modern and traditional adjuvants. The immunization schedules varied depending upon the adjuvant manufacturer's recommendations and details are included in Table 2. Animals were bled following the full course of immunization and sera analyzed for antibody responses. Antibodies which were able to bind to 80%E were detected by indirect ELISA assay using DEN-2 80%E as coating antigen. Neutralizing antibodies were assayed using a plaque reduction neutralization test (PRNT) where the highest dilution of sera which resulted in at least 80% reduction in number of plaques compared to a control is reported as the $PRNT_{80}$ titer. The results are summarized in Table 2. Briefly, several of the adjuvants, including MF75, RIBI, and iscom matrix, induced potent virus neutralizing antibody responses. MF59, Freund's adjuvant, and Alum on the other hand induced high titer 80%E binding antibodies but low titer neutralizing responses. This is despite the fact that these adjuvants have been shown to work well with a variety of other immunogens. This demonstrates the empiric nature of establishing effectiveness of adjuvant-subunit formulations, that is effective formulations can not be predicted based on reports in the literature but must be determined experimentally.

TABLE 2

Effect of Adjuvants on Immunogenicity of DEN-2 80% E in Adult Mice

| Adjuvant | Immunogen/Schedule | ELISA Titer | $PRNT_{80}$ Titer |
|---|---|---|---|
| MF59 adjuvant | 25 $\mu$g DEN-2 80% E, day 0<br>12.5 $\mu$g DEN-2 80% E, day 21<br>12.5 $\mu$g DEN-2 80% E, day 42<br>subcutaneous inoculation | 25,600 | 26 |
| MF75 adjuvant | 25 $\mu$g DEN-2 80% E, day 0<br>12.5 $\mu$g DEN-2 80% E, day 21<br>12.5 $\mu$g DEN-2 80% E, day 42<br>subcutaneous inoculation | 102,000 | 2298 |
| RIBI adjuvant | 25 $\mu$g DEN-2 80% E, day 0<br>12.5 $\mu$g DEN-2 80% E, day 21<br>12.5 $\mu$g DEN-2 80% E, day 42<br>subcutaneous inoculation | 25,600 | 333 |
| Alum<br>(aluminum hydroxide) | 25 $\mu$g DEN-2 80% E, day 0<br>12.5 $\mu$g DEN-2 80% E, day 21<br>12.5 $\mu$g DEN-2 80% E, day 42<br>subcutaneous inoculation | 8445 | 24 |
| Freund's complete adjuvant<br>Freund's incomplete adjuvant<br>Freund's incomplete adjuvant | 25 $\mu$g DEN-2 80% E, day 0<br>12.5 $\mu$g DEN-2 80% E, day 21<br>12.5 $\mu$g DEN-2 80% E, day 42<br>intraperitoneal inoculation | 36,204 | <10 |
| ISCOMATRIX ™ adjuvant | 10 $\mu$g DEN-2 80% E, day 0<br>10 $\mu$g DEN-2 80% E, day 28<br>subcutaneous inoculation | 25,600 | 4000 |
| no adjuvant | 25 $\mu$g DEN-2 80% E, day 0<br>12.5 $\mu$g DEN-2 80% E, day 21<br>12.5 $\mu$g DEN-2 80% E, day 42<br>subcutaneous inoculation | 8445 | 11 |

TABLE 2-continued

Effect of Adjuvants on Immunogenicity of DEN-2 80% E in Adult Mice

| Adjuvant | Immunogen/Schedule | ELISA Titer | $PRNT_{80}$ Titer |
|---|---|---|---|
| PBS | PBS only, day 0<br>PBS only; day 21<br>PBS only, day 42<br>Subcutaneous inoculation | <100 | <10 |

EXAMPLE 12

Dose Response to DEN-2 80%E in ISCOMATRIX and Freund's Adjuvants

Figure 4:
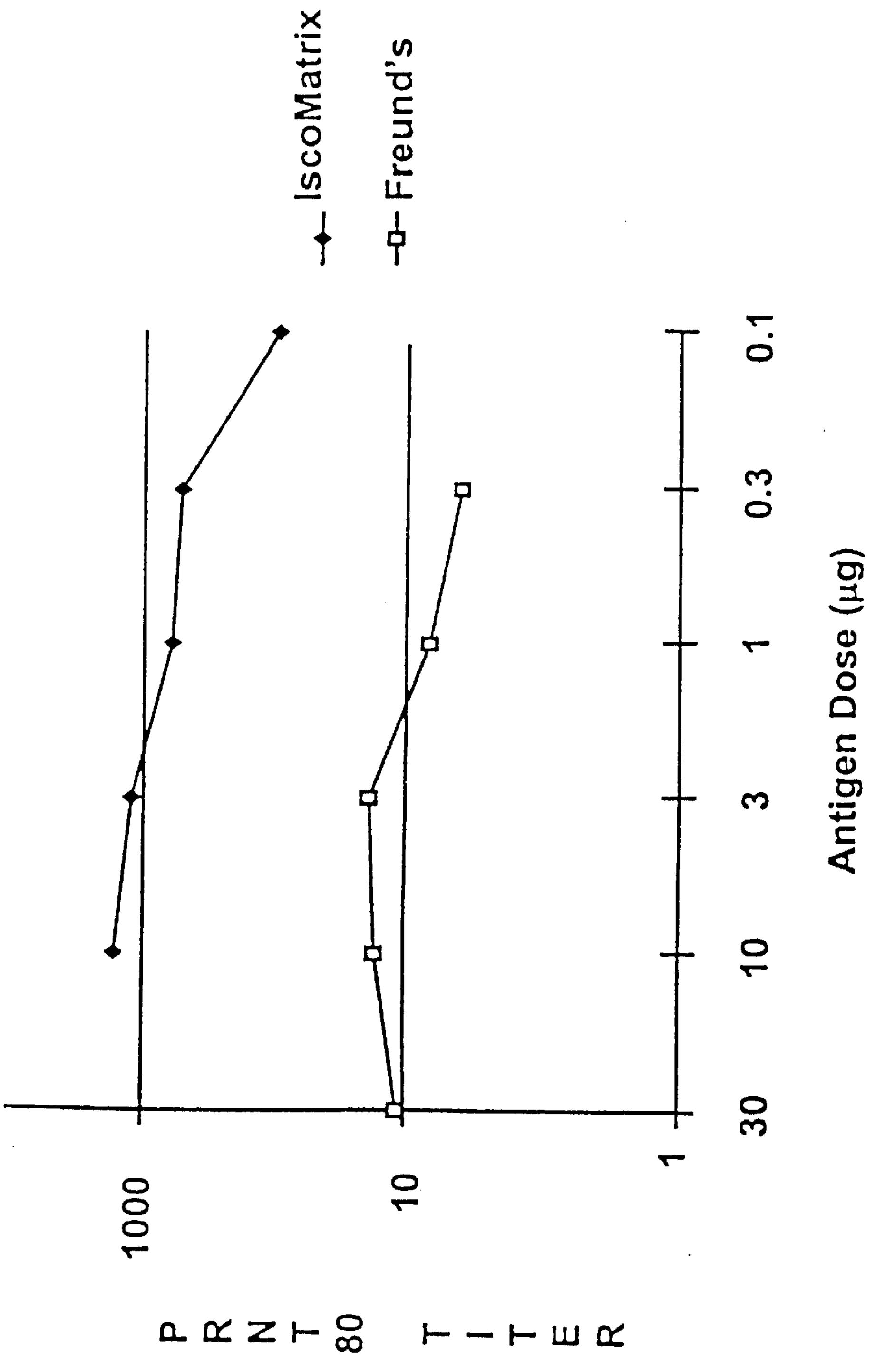
FIG. 4 shows the dose response of adult mice to pure 80%E administered in iscom matrix and Freund's.

In order to demonstrate the dose-dependent nature of the immune response to the recombinant 80%E product, adult mice were immunized with various doses of DEN-2 80%E in either Freund's adjuvant or ISCOMATRIX. Mice immunized with Freund's adjuvant received three doses given at two week intervals, with the two booster doses being one half of the priming dose and administered in Freund's incomplete adjuvant. The mice immunized with the recombinant product in ISCOMATRIX received two equivalent doses administered in 10 μg of ISCOMATRIX at 28 day intervals. The neutralizing antibody titers obtained are shown in FIG. 4. Specifically this figure shows the dose response of mice immunized with DEN-2 80%E in ISCOMATRIX or Freund's adjuvant. Neutralizing antibody titers were determined post-immunization with various doses of DEN-2 80%E in either ISCOMATRIX or Freund's adjuvants. Geometric mean $PRNT_{80}$ titers are plotted versus antigen dose for both adjuvants. A dose response is apparent with both adjuvants although the response in Freund's adjuvant appears to plateau at ~3 μg of protein. Clearly the virus neutralizing antibody response is much more potent in ISCOMATRIX adjuvant.

EXAMPLE 13

Immune Response of Mice Immunized with Purified 80%E from all Four Dengue Serotypes in ISCOMATRIX DEN-1–4 80%E antigens purified by hydroxyapatite/size exclusion chromatography (HTP/SEC) or immunoaffinity chromatography were used to immunize adult female BALB/c mice. Mice (five mice per experimental group) were inoculated subcutaneously with 10 μg purified 80%E antigen and 10 μg ISCOMATRIX™ adjuvant in 100 μl PBS. Two injections were given 28 days apart, and sera were collected 10 days following the second immunization. Sera from mice immunized with DEN-2 80%E were serially diluted and analyzed by ELISA using microtiter plates coated with purified DEN-2 80%E. Sera from mice immunized with DEN-1, -3, and -4 80%E were tested in a capture ELISA, in which plates coated with rabbit anti-dengue virus antibodies were used to capture the homologous recombinant DEN-80%E antigen. Sera were also tested for the presence of neutralizing antibodies against the homologous virus, by the plaque reduction neutralization method. Geometric mean ELISA titers and serum neutralizing antibody responses (80% plaque reduction) are summarized in Table 3.

TABLE 3

Geometric Mean ELISA and neutralizing antibody titers of BALB/c mice immunized with purified DEN 80% E antigens in combination with ISCOMATRIX ™ adjuvant.

| Purification | Antigen | | | | | | | |
|---|---|---|---|---|---|---|---|---|
| | DEN-1 80% E | | DEN-2 80% E | | DEN-3 80% E | | DEN-4 80% E | |
| Method | ELISA | $PRNT_{80}$ | ELISA | $PRNT_{80}$ | ELISA | $PRNT_{80}$ | ELISA | $PRNT_{80}$ |
| HTP/SEC | 3676 | 5248 | 77,605 | 12,023 | 25,600 | 1143 | 6400 | 552 |
| IAC | 1600 | 7943 | 178,289 | 9,120 | 19,401 | 565 | 19,401 | 174 |

EXAMPLE 14

Dose-response Relationship of Purified DEN-1–4 80%E Antigens in Adult Mice Using ISCOMATRIX Adult female BALB/c mice were immunized with increasing amounts of immunoaffinity purified DEN 80%E antigens administered with 10 μg ISCOMATRIX™ (Iscotec AB, Sweden) adjuvant. Mice were immunized twice, 28 days apart, by the subcutaneous route. Sera were collected 10 days following the second immunization and evaluated for antibody titer by ELISA (DEN-2 80%E coated directly on plate) or by MAb 4G2 antigen capture ELISA (DEN-1, -3) and for virus neutralizing antibody titer against the homologous virus by plaque reduction neutralization test (Table 4). A clear dose response is seen with DEN-1, DEN-2, and DEN-4 80%E. With DEN-3 80%E a plateau is reached at approximately a 1 μg dose above which no significant increase in titer is observed.

TABLE 4

ELISA and neutralizing antibody titers of BALB/c mice immunized with various doses of DEN 80% E antigens in combination with ISCOMATRIX ™ adjuvant.

| Antigen dose | Antigen | | | | | | | |
|---|---|---|---|---|---|---|---|---|
| | DEN-1 80% E | | DEN-2 80% E | | DEN-3 80% E | | DEN-4 80% E | |
| ($\mu$g) | ELISA | $PRNT_{80}$ | ELISA | $PRNT_{80}$ | ELISA | $PRNT_{80}$ | ELISA | $PRNT_{80}$ |
| 30 | NT | NT | NT | NT | 28,813 | 1741 | NT | 728 |
| 10 | 21,200 | 1450 | 77,605 | 10,554 | 89,144 | 1550 | NT | 526 |
| 3 | 29,407 | 1053 | 51,200 | 8572 | 89,144 | 1908 | NT | 278 |
| 1 | 25,600 | 504 | 51,200 | 4594 | 102,400 | 1414 | NT | 144 |
| 0.3 | 4222 | 35 | 29,407 | 2095 | 16,890 | 400 | NT | 28 |
| 0.1 | <151 | <20 | 7352 | 590 | NT | NT | NT | NT |

NT—Not tested.
*DEN-4 PRNT titers reported as $PRNT_{50}$ titers while others reported as $PRNT_{80}$ titers. This reflects a change in protocol which occurred in order to adapt to the standard used by the rest of the dengue field. The actual titration includes an additional two-fold dilution compared to the PRNT80 protocol and hence the numbers obtained using our $PRNT_{80}$ and the new $PRNT_{50}$ protocols are comparable.

EXAMPLE 15

Figure 5:
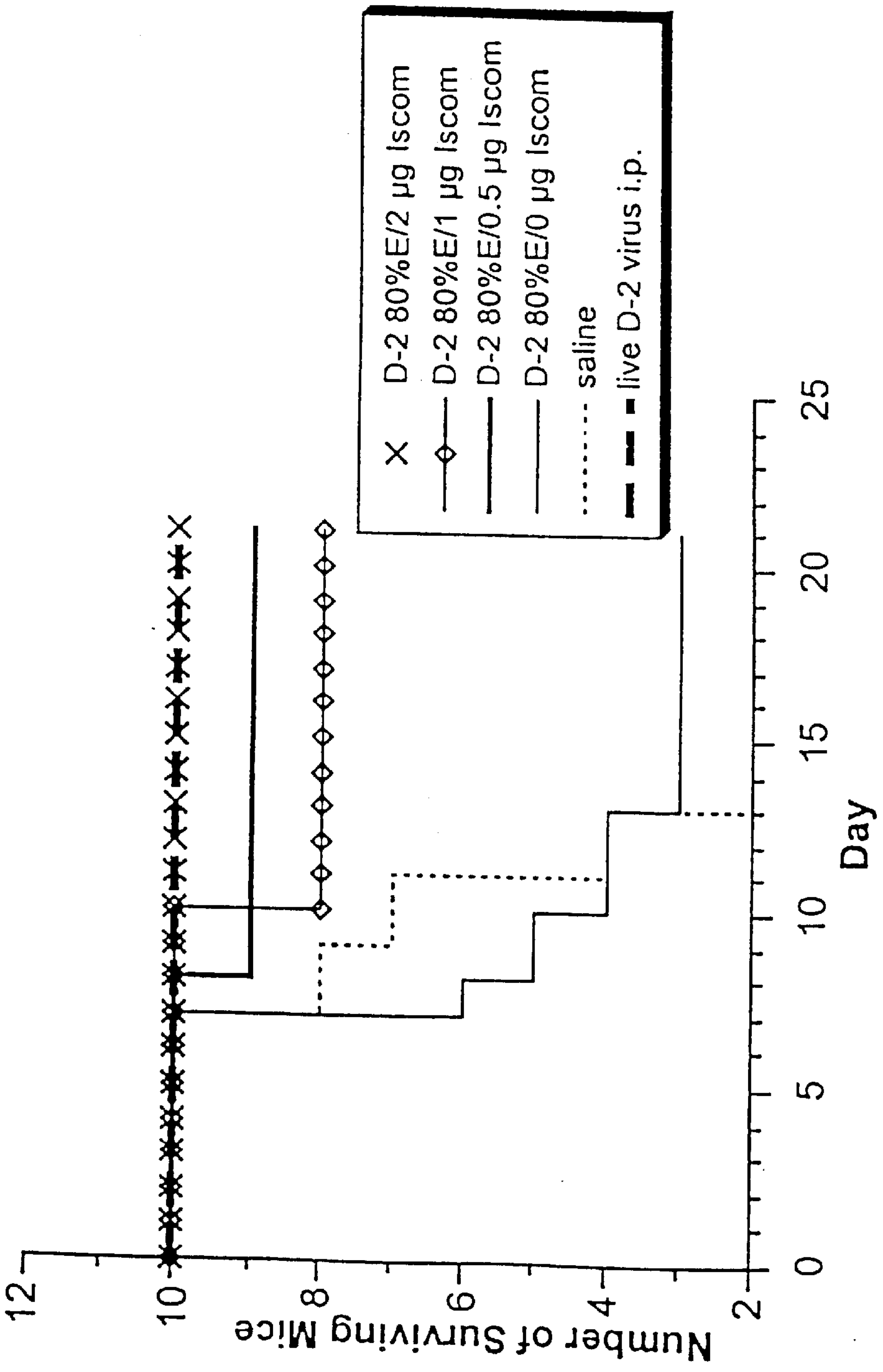
FIG. 5 shows the survival of mice immunized with DEN-2 80%E in iscom matrix.

Protection from Viral Challenge of Suckling Mice Immunized with DEN-2 80%E in ISCOMATRIX Suckling mice were administered a subcutaneous priming dose of DEN-2 80%E and ISCOMATRIX™ adjuvant in PBS. A booster inoculation was given two weeks later, and this was followed by an intracranial DEN-2 viral challenge (100 $LD_{50}$ doses) one week later. Mice were monitored for 21 days post-challenge for signs of morbidity and mortality. This experiment included the following test groups:

1. DEN-2 80%E (5 $\mu$g/dose)+2 $\mu$g ISCOMATRIX™ adjuvant
2. DEN-2 80%E (5 $\mu$g/dose)+1 $\mu$g ISCOMATRIX™ adjuvant
3. DEN-2 80%E (5 $\mu$g/dose)+0.5 $\mu$g ISCOMATRIX™ adjuvant
4. DEN-2 80%E (5 $\mu$g/dose) in saline
5. positive control, $5\times10^5$ particle forming units of live DEN-2 virus (S16803)
6. negative control, PBS Results of the challenge study are depicted in FIG. 5, which shows survival of immunized mice after challenge with live dengue-2 virus. Following immunization with DEN-2 80%E administered in various doses of ISCOMATRIX™ adjuvant, saline (negative control), or with live DEN-2 virus administered (positive control), mice were challenged intracranially with 100 $LD_{50}$ doses of DEN-2 virus (New Guinea C). Day 0 is the day of viral challenge. DEN-2 80%E in 2 $\mu$g ISCOMATRIX™ and the subcutaneous live DEN-2 viral positive control afforded complete protection from neurotropic viral challenge, with no signs of morbidity. Decreasing amounts of adjuvant resulted in decreased protection.

EXAMPLE 16

Partial Protection of Suckling Mice Immunized with JEV 80%E in ISCOMATRIX

Three week old ICR or Balb/c mice were immunized subcutaneously with 8 $\mu$g of JEV 80%E with 2 $\mu$g of ISCOMATRIX adjuvant. Some animals were boosted 21 days later with the same dose. Seven days post-boost the animals were challenged by intracranial injection with 100 $LD_{50}$ (50,000 pfu) virulent JEV virus. The results are summarized in Table 5. The virus binding response was monitored by ELISA and is recorded as the optical density obtained with a 1:400 dilution of serum. The virus neutralizing response is recorded as the $PRNT_{75}$ titer. While the PRNT titers are lower than that obtained with the dengue antigens, this represents an unoptimized immunization schedule with baby mice whose immune system has not yet matured. Even so, titers of this magnitude are not atypical of other efficacious JEV vaccines. Likewise, the protection from viral challenge, while not complete, demonstrates significant enhancement compared to control animals at least for a two dose regimen in ICR mice.

TABLE 5

Immune Response and Protection from Challenge in Mice Immunized with JEV 80% E

| | | | Day 21 Dose 2 | | Day 28 Challenge | | Day 63 5 wk post chall. | | |
|---|---|---|---|---|---|---|---|---|---|
| Group | Vaccine | Day 0 Dose 1 | Serum OD @ 1:400 | PRNT 75 | Serum OD @ 1:400 | PRNT 75 | Serum OD @ 1:400 | PRNT 75 Survivor | % Survival |
| ICR 1 dose | 8 $\mu$g JEV 80% E 2 $\mu$g ISCOMATRIX | NT | 1.23 | <10 | 1.46 | <10 | NT | 640 | 20 |
| ICR 2 dose | 8 $\mu$g JEV 80% E 2 $\mu$g ISCOMATRIX | NT | 1.36 | <10 | 2.27 | 20 | NT | 320 | 50 |
| Balb/c 2 dose | 8 $\mu$g JEV 80% E 2 $\mu$g ISCOMATRIX | NT | 0.55 | <10 | 2.04 | 20 | NT | 190 | 30 |

TABLE 5-continued

Immune Response and Protection from Challenge in Mice Immunized with JEV 80% E

| Group | Vaccine | Day 0 Dose 1 | Day 21 Dose 2 Serum OD @ 1:400 | Day 21 Dose 2 PRNT 75 | Day 28 Challenge Serum OD @ 1:400 | Day 28 Challenge PRNT 75 | Day 63 5 wk post chall. Serum OD @ 1:400 | Day 63 5 wk post chall. PRNT 75 Survivor | % Survival |
|---|---|---|---|---|---|---|---|---|---|
| ICR Negative control | PBS only | NT | 0.04 | <10 | 0.07 | <10 | NT | NT | 0 |
| ICR Negative Control | PBS 2 μg ISCOMATRIX | NT | 0.04 | <10 | 0.05 | <10 | NT | NT | 0 |

EXAMPLE 17

Figure 6:
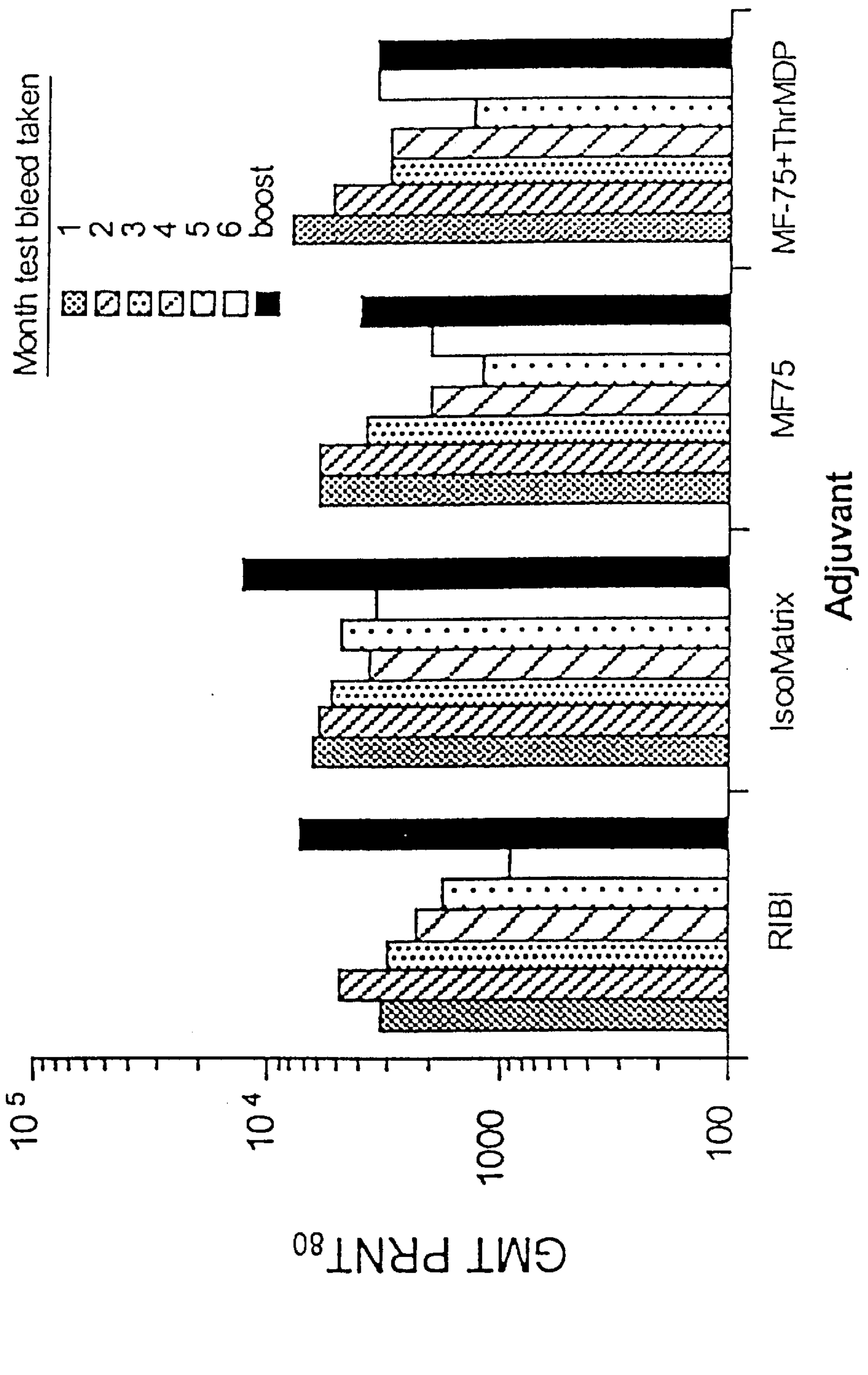
FIG. 6 demonstrates the duration of immunity of mice immunized with DEN-2 80%E in several adjuvants.
Figure 7A:
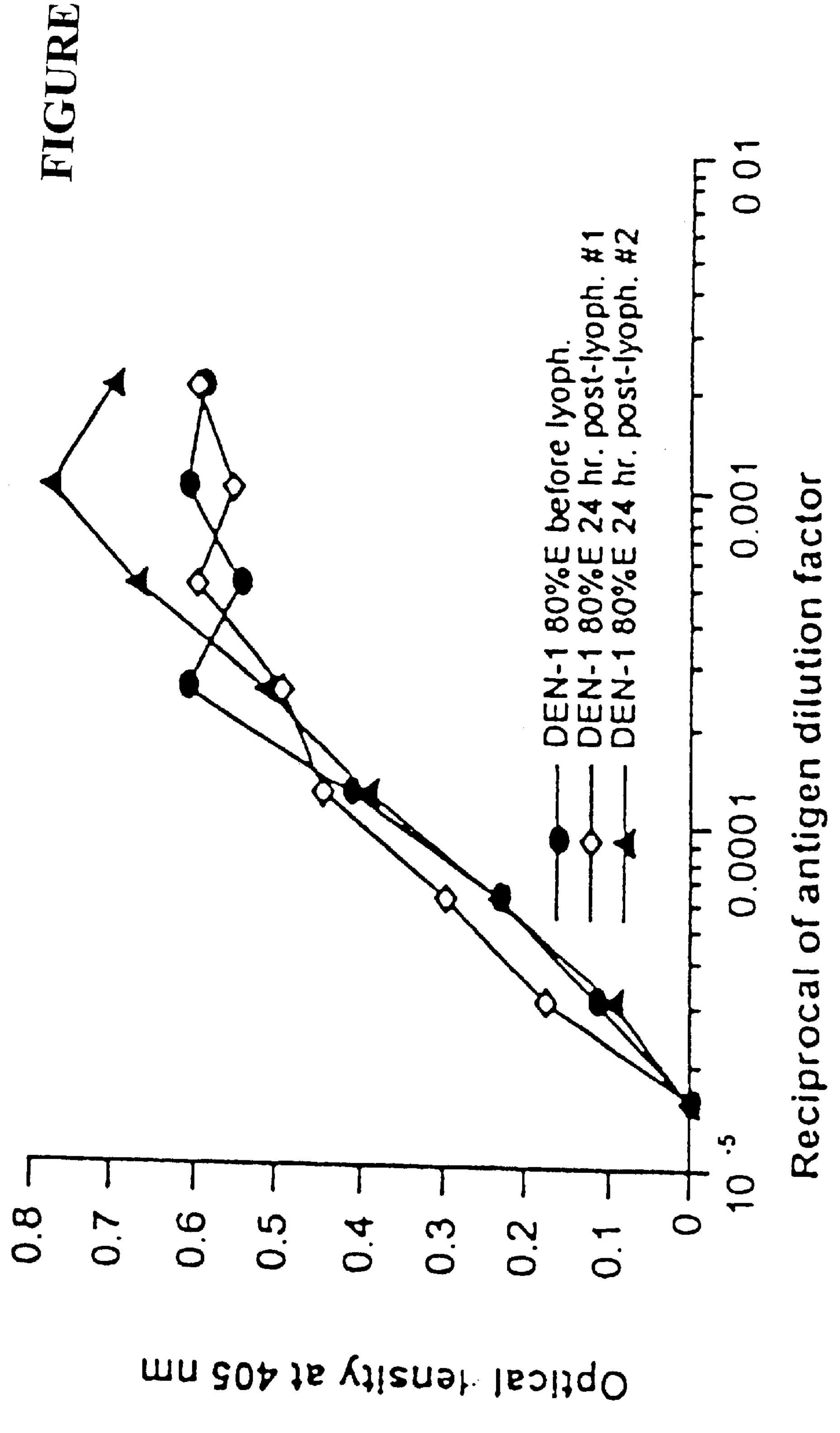
FIGS. 7A–D compare the lack of product loss and lack of loss of immunoreactivity of both pre- and post-lyophilization samples containing DEN-2 80%E.
Figure 7B:
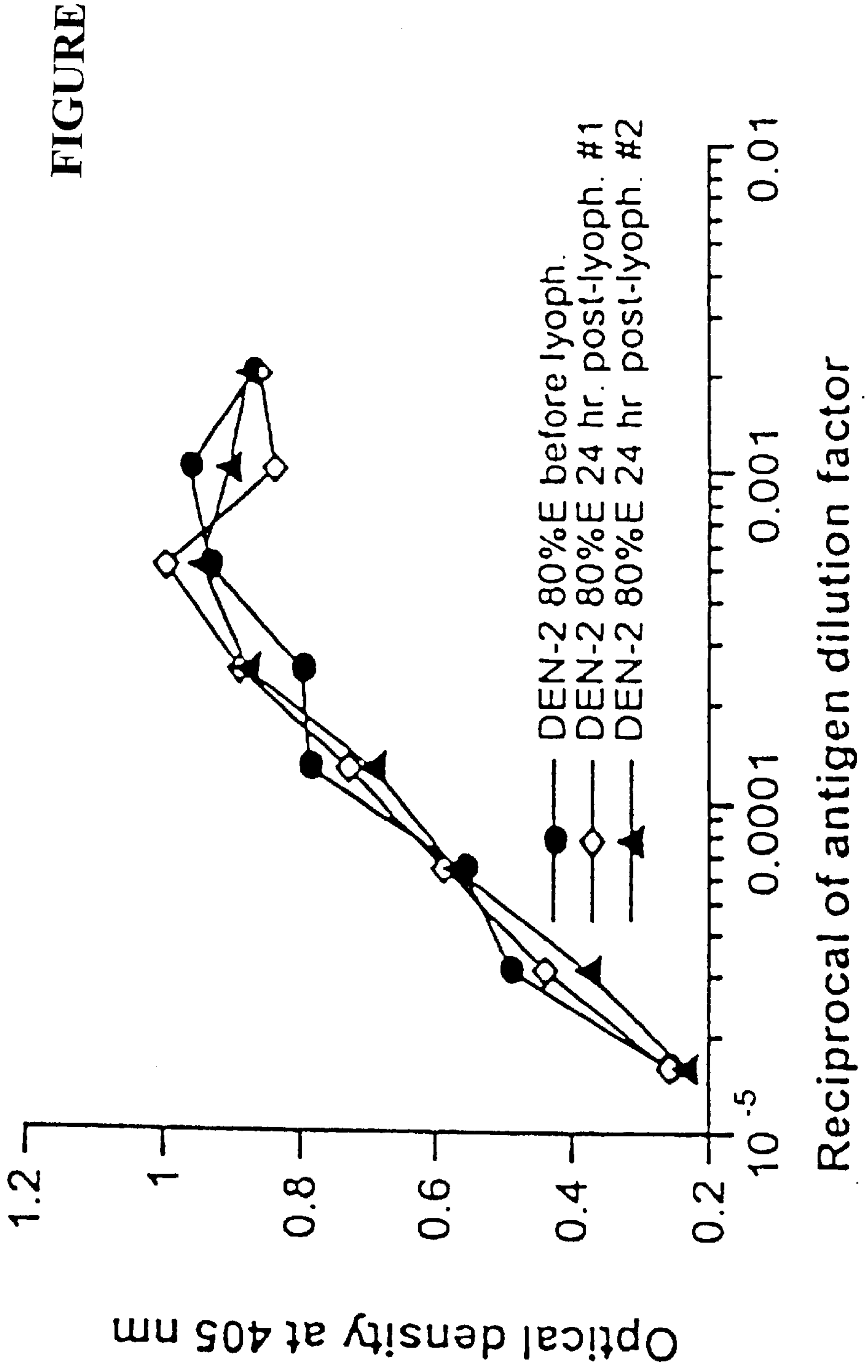
Figure 7C:
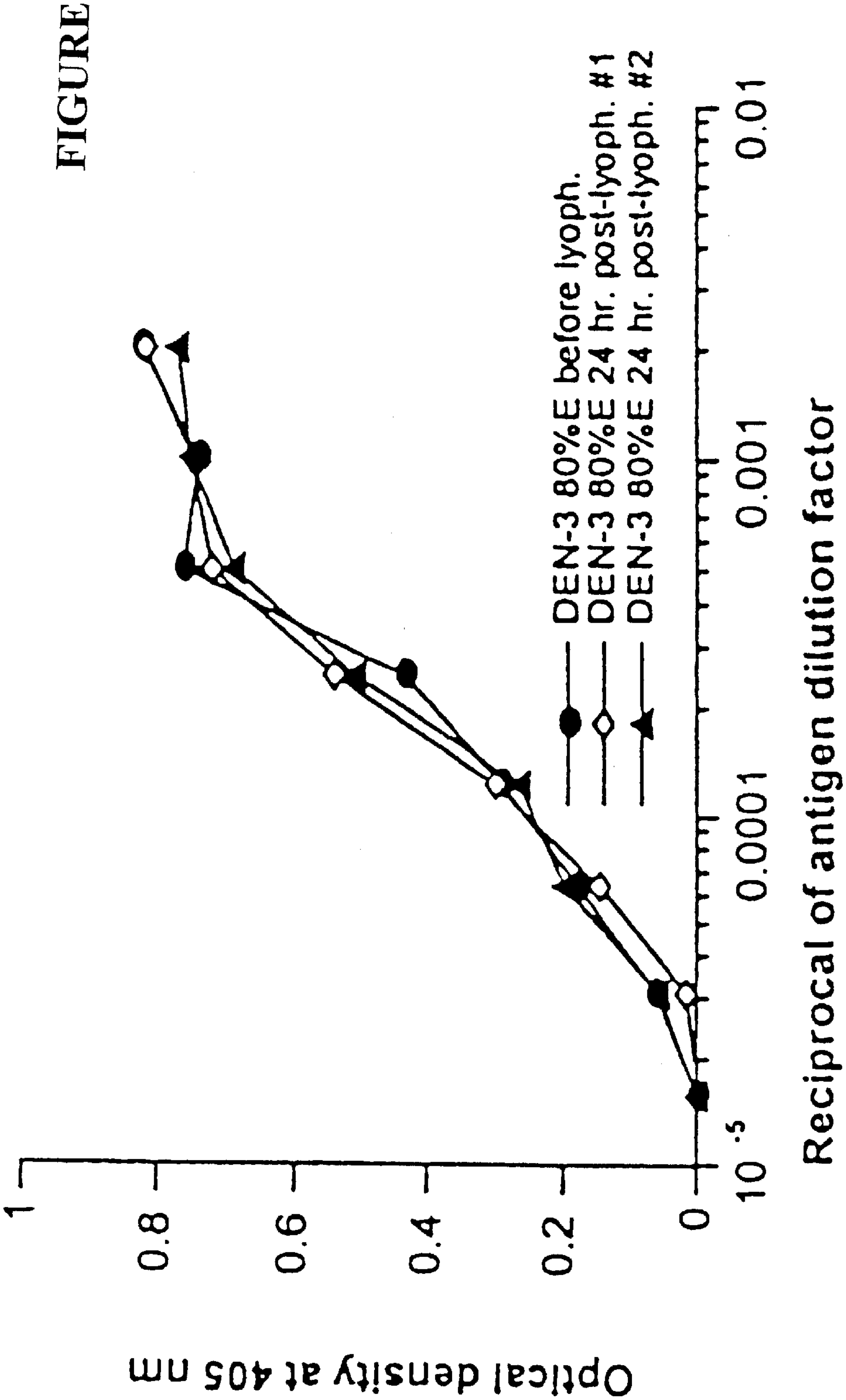
Figure 7D:
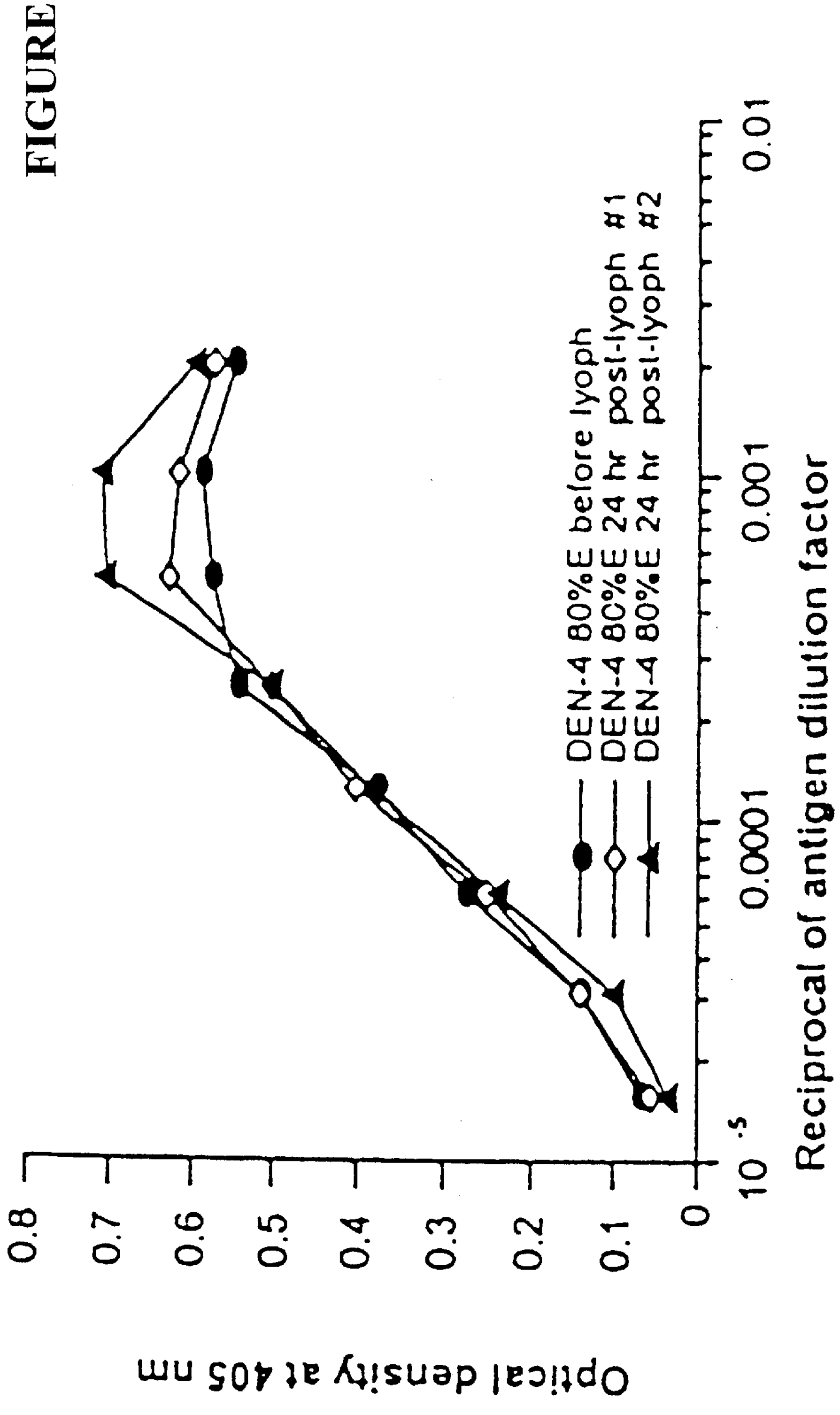

Duration of Immunity Induced by Immunization with DEN-2 80%E in Various Adjuvants DEN-2 80%E was administered to adult female BALB/c mice according to the following schedules: (a) RIBI: day 0, 25 μg 80%E in 0.2 ml RIBI MPL+TDM (0.1 ml s.c. scapular region; 0.1 ml s.c. hind leg); day 21, as above with 12.5 μg 80%E; day 42, same as day 21; 6 mo. boost, as day 21 & 42. (b) ISCOMATRIX™: day 0,10 μg 80%E+10 μg ISCOMATRIX™, 0.1 ml s.c. scapular; day 28, as day 0; 6 mo. as day 0. (c ) MF-75: day 0, 1:1 dilution of antigen into adjuvant Schedule the same as for RIBI, except 0.1 ml volume administered s.c. to scapular region. (d) MF-75+ ThrMDP: same as MF-75, with 40 μg ThrMDP per dose. Test bleeds were taken at monthly intervals for six months following the initial prime/boost regimen described above. At six months, a final booster inoculation was given as described above, and a final test bleed taken 10 days later. All test bleeds were tested by plaque reduction neutralization test, and the $PRNT_{80}$ titer determined. The results are summarized in FIG. 6, which shows the duration of immunity to DEN-2 80%E administered in various adjuvants listed above.

EXAMPLE 18

Tetravalent Response Induced by Immunization of Mice with 80%E from all Four Dengue Serotypes The virus neutralizing antibody responses to immunoaffinity purified DEN-1, -2, -3, and -4 80%E antigens or equal weight combinations of DEN-1–4 80%E was determined in adult female BALB/c mice. Mice were immunized subcutaneously with either 10 μg or 2.5 μg of DEN-1, -2, -3, or -4 80%E (5 mice per group), or combinations of 10 μg each of all four antigens (10 mice per group). Each 0.1 ml dose also contained 10 μg ISCOMATRIX™ adjuvant and PBS diluent. A booster immunization was given after four weeks, and sera were collected 10 days later. A summary of the neutralizing antibody titers of mice receiving 10 μg doses of the individual serotype 80%E antigens or the tetravalent dengue vaccine in IscoMatrix™ is shown in Table 6. These results demonstrate that neutralizing antibody responses to each virus are induced by the homologous 80%E antigen, and importantly, this response is maintained when the antigen is presented in a tetravalent formulation.

TABLE 6

Geometric mean neutralizing antibody titer of mice immunized with DEN-1–4 80% E antigens separately or as a tetravalent admixture (10 μg per antigen)

| Immunogen | DEN-1 $PRNT_{80}$ Geometric Mean | DEN-2 $PRNT_{80}$ Geometric Mean | DEN-3 $PRNT_{80}$ Geometric Mean | DEN-4 $PRNT_{80}$ Geometric Mean |
|---|---|---|---|---|
| 10 μg DEN-1 80% E 10 μg ISCOMATRIX | 2759 | NT | NT | NT |
| 10 μg DEN-2 80% E 10 μg ISCOMATRIX | NT | 3031 | NT | NT |
| 10 μg DEN-3 80% E 10 μg ISCOMATRIX | NT | NT | 381 | NT |
| 10 μg DEN-4 80% E 10 μg ISCOMATRIX | NT | NT | NT | 174 |
| 10 μg each DEN-1 80% E DEN-2 80% E DEN-3 80% E DEN-4 80% E 10 μg ISCOMATRIX | 1589 | 2639 | 564 | 159 |
| PBS 10 μg ISCOMATRIX | <20 | <20 | <20 | <20 |

NT—not tested

EXAMPLE 19

Immunization of Rhesus Monkeys with DEN-2 80%E Administered in ISCOMATRIX™ Adjuvant A study in Rhesus monkeys (*Macaca mulatta*) was performed in order to estimate an effective DEN-2 80%E and ISCOMATRIX formulation. The endpoints for this study were a) elicitation of serum virus neutralizing antibodies, as determined by in vitro viral plaque reduction assay, and b) reduction in dengue viremia following live virus challenge. Eleven monkeys were used in this experiment. Rhesus monkeys designated by animal ID were vaccinated by subcutaneous inoculation with the indicated vaccines on study day 0 and boosted on study days 34 and 97. The ISCOMATRIX formulations included 50 μg of adjuvant. In the alum formulation, Aluminum hydroxide (alum) adjuvant from Reheis, Inc at 0.1% was adsorbed with antigen for 1 hr prior to administration. Dengue-2 purified inactivated vaccine (PIV) from WRAIR (laboratory lot 9, May 97) was diluted 1:4 in PBS prior to administration. On study day 132, all animals were challenged with $10^4$ pfu live dengue-2 virus (S16803 Parental strain) and viremia determinations were carried out for 12 days post-challenge. Results of the neutralizing antibody analysis are shown in Table 7. High titer neutralizing antibody responses were induced by all formulations following the three dose regimen. Particularly high titer responses were detected in the monkeys receiving the 5 μg dose of DEN-2 80%E antigen in ISCOMATRIX.

On study day 132 all animals were challenged with $10^4$ plaque forming units of live dengue-2 virus (Strain S16803 Parent). Blood samples were drawn daily for 12 days and the sera (0.1 ml) were inoculated onto C6/36 cells. The inoculated cells were incubated at 28 ° C. for 14 days to amplify any virus present. Virus was then detected by plaque assay of 0.2 ml of C6/36 cell culture fluid on Vero cell monolayers. Serum samples which were positive for virus using the C6/36 amplification assay were then directly titered by plaquing on Vero cell monolayers. The results of the viremia studies are shown in Table 8. Complete suppression of viremia was achieved with 5 μg DEN-2 80%E in combination with 50 μg ISCOMATRIX™ adjuvant demonstrating vaccine efficacy in non-human primates.

TABLE 7

Neutralizing antibody titers of Rhesus monkeys immunized with DEN-2 80% E in ISCOMATRIX ™ adjuvant

| ID | Vaccine | DEN-2 $PRNT_{50}$ Antibody Titer on Study Day: | | | | | | | |
|---|---|---|---|---|---|---|---|---|---|
| | | Day 0 Vacc. | Day 34 Vacc. | Day 49 | Day 69 | Day 97 Vacc. | Day 113 | Day 132 Challenge | Day 159 |
| G617 | 100 μg DEN-2 80% E ISCOMATRIX | <10 | 10 | 180 | 460 | 230 | 920 | 400 | >12,800 |
| B7487 | 100 μg DEN-2 80% E ISCOMATRIX | <10 | 110 | 480 | 480 | 600 | >640 | >640 | >12,800 |
| F477 | 25 μg DEN-2 80% E ISCOMATRIX | <10 | <10 | 300 | 230 | 450 | 660 | 660 | >12,800 |
| I613 | 25 μg DEN-2 80% E ISCOMATRIX | <10 | 90 | 3,000 | 1,000 | 1,100 | >1,280 | >1,280 | >12,800 |
| I619 | 5 μg DEN-2 80% E ISCOMATRIX | <10 | 50 | 1,600 | 590 | 1,900 | >1,280 | 1,200 | >12,800 |
| H7J | 5 μg DEN-2 80% E ISCOMATRIX | <10 | 10 | 620 | 760 | 530 | >1,280 | >640 | >12,800 |
| F485 | 100 μg DEN-2 80% E alum[d] | <10 | 60 | 650 | 1,200 | 250 | 770 | 600 | >12,800 |
| 517Z | PIV[e] 1:4 alum | <10 | <10 | 120 | 320 | 90 | 490 | 50 | 8,000 |
| N637 | None | ND | ND | ND | ND | ND | ND | <10 | 860 |
| N670 | None | ND | ND | ND | ND | ND | ND | <10 | 1,600 |
| N816 | None | ND | ND | ND | ND | ND | ND | <10 | 990 |

TABLE 8

Dengue Viremia in Vaccinated Rhesus Monkeys After Challenge with Live Dengue 2 Virus

| Monkey ID | Vaccine | Viremia[a)] on day: 1 | 2 | 3 | 4 | 5 | 6 | 7 | 8 | 9 | 10 | 11 | 12 |
|---|---|---|---|---|---|---|---|---|---|---|---|---|---|
| G617 | 100 μg DEN-2 80% E 50 μg ISCOMATRIX ™ | 0 | 0 | 0 | 0 | 0 | 0 | + | + | 0 | 0 | 0 | 0 |
| B7487 | 100 μg DEN-2 80% E 50 μg ISCOMATRIX ™ | 0 | 0 | 0 | 0 | 0 | + | + | + | 0 | 0 | 0 | 0 |

TABLE 8-continued

Dengue Viremia in Vaccinated Rhesus Monkeys After Challenge with Live Dengue 2 Virus

| Monkey ID | Vaccine | Viremia[a)] on day: 1 | 2 | 3 | 4 | 5 | 6 | 7 | 8 | 9 | 10 | 11 | 12 |
|---|---|---|---|---|---|---|---|---|---|---|---|---|---|
| F477 | 25 μg DEN-2 80% E 50 μg ISCOMATRIX ™ | 0 | 0 | 0 | + | + | + | + | + | 0 | 0 | 0 | 0 |
| I613 | 25 μg DEN-2 80% E 50 μg ISCOMATRIX ™ | 0 | 0 | 0 | 0 | 0 | + | 0 | 0 | 0 | 0 | 0 | 0 |
| I619 | 5 μg DEN-2 80% E 50 μg ISCOMATRIX ™ | 0 | 0 | 0 | 0 | 0 | 0 | 0 | 0 | 0 | 0 | 0 | 0 |
| H7J | 5 μg DEN-2 80% E 50 μg ISCOMATRIX ™ | 0 | 0 | 0 | 0 | 0 | 0 | 0 | 0 | 0 | 0 | 0 | 0 |
| F485 | 100 μg DEN-2 80% E 0.1% alum | 0 | 0 | 0 | 0 | 0 | 0 | + | + | + | + | 0 | 0 |
| 517Z | PIV + 0.1% alum | 0 | 0 | 0 | 0 | 0 | 0 | 0 | 0 | 0 | 0 | 0 | 0 |
| N637 | None | 0 | + | + | + | + | + | + | + | + | 0 | 0 | + |
| N670 | None | 0 | + | + | ? | + | + | + | + | + | + | + | 0 |
| N816 | None | 0 | + | + | + | ? | + | + | 0 | + | + | 0 | 0 |

[a)]+ = approximately 100 or greater virus plaques;
? = one to five virus plaques;
0 = no virus plaques.

EXAMPLE 20

Lyophilization of DEN-2 80%E and ISCOMATRIX

Stability of any vaccine is critical to its successful practice and therefore the stability of the recombinant 80%E product is an important component of its patentability. Therefore, we demonstrated that purified 80%E can be stored in a lyophilized form, which is stable at room temperature, and it maintains full immunogenicity in ELISA and mouse testing.

Aliquots (200 μl) of purified DEN-2 80%E antigen were lyophilized from a 0.525 mg/ml solution in 10 mM sodium phosphate, pH 7.0, and 5% (w/v) sucrose, trehalose, or lactose excipient. The samples were frozen on dry ice-acetone and lyophilized at −34° C. under a pressure of 45 mT for 19 hr. The shelf temperature was then ramped to 25° C. over a period of 400 minutes, in increments of 5° C.×30 min. Samples were dried for 19 hr at 25° C., and sealed under vacuum Comparison of pre- and post-lyophilization samples by SDS-PAGE and ELISA demonstrated no product loss or change in immunoreactivity resulting from lyophilization. FIGS. 7A–7D show the ELISA activity of DEN-1–4 80%E, respectively, following lyophilization. Trials for each serotype 80%E were done in duplicate (i.e. #1 and #2) at a starting concentration of 0.5 mg/ml in 10 mM phosphate (pH 7.2) containing 5% (w/v) lactose. Samples were frozen at −35° C. and lyophilized overnight at −33° C. with secondary drying under vacuum at 25° C. Freeze-dried cakes were reconstituted to the starting condition by adding water and compared to matched samples that were not subjected to lyophilization in sandwich ELISA assays. The ELISA involved sandwiching analyte between a 9D12 MAb coat and a secondary polyclonal rabbit serum raised against DEN-2 domain B (E138-2).

Figure 8A:
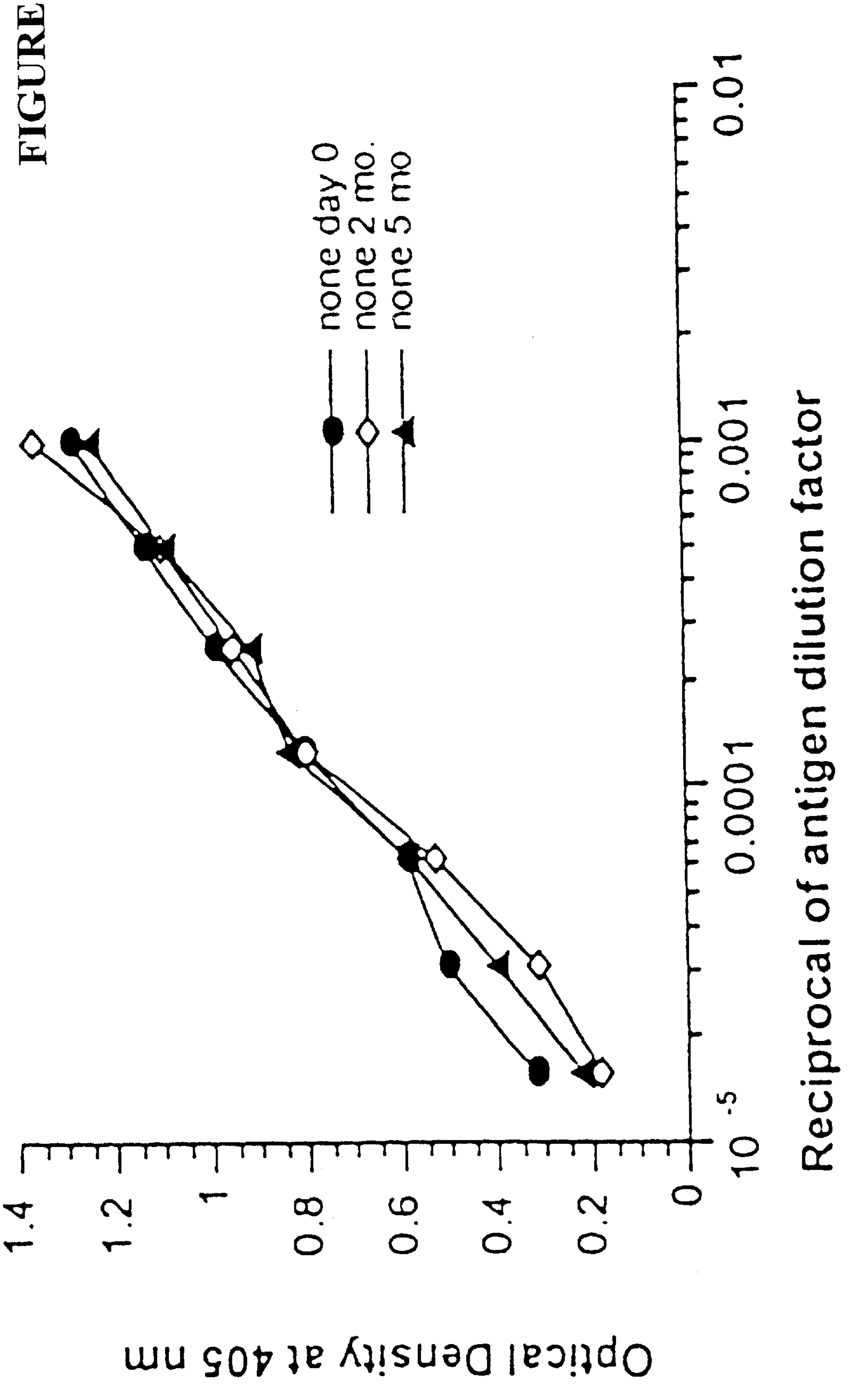
FIGS. 8A–C compare the stability of lyophilized DEN-2 80%E without excipients and with sucrose or trehalose excipients.
Figure 8B:
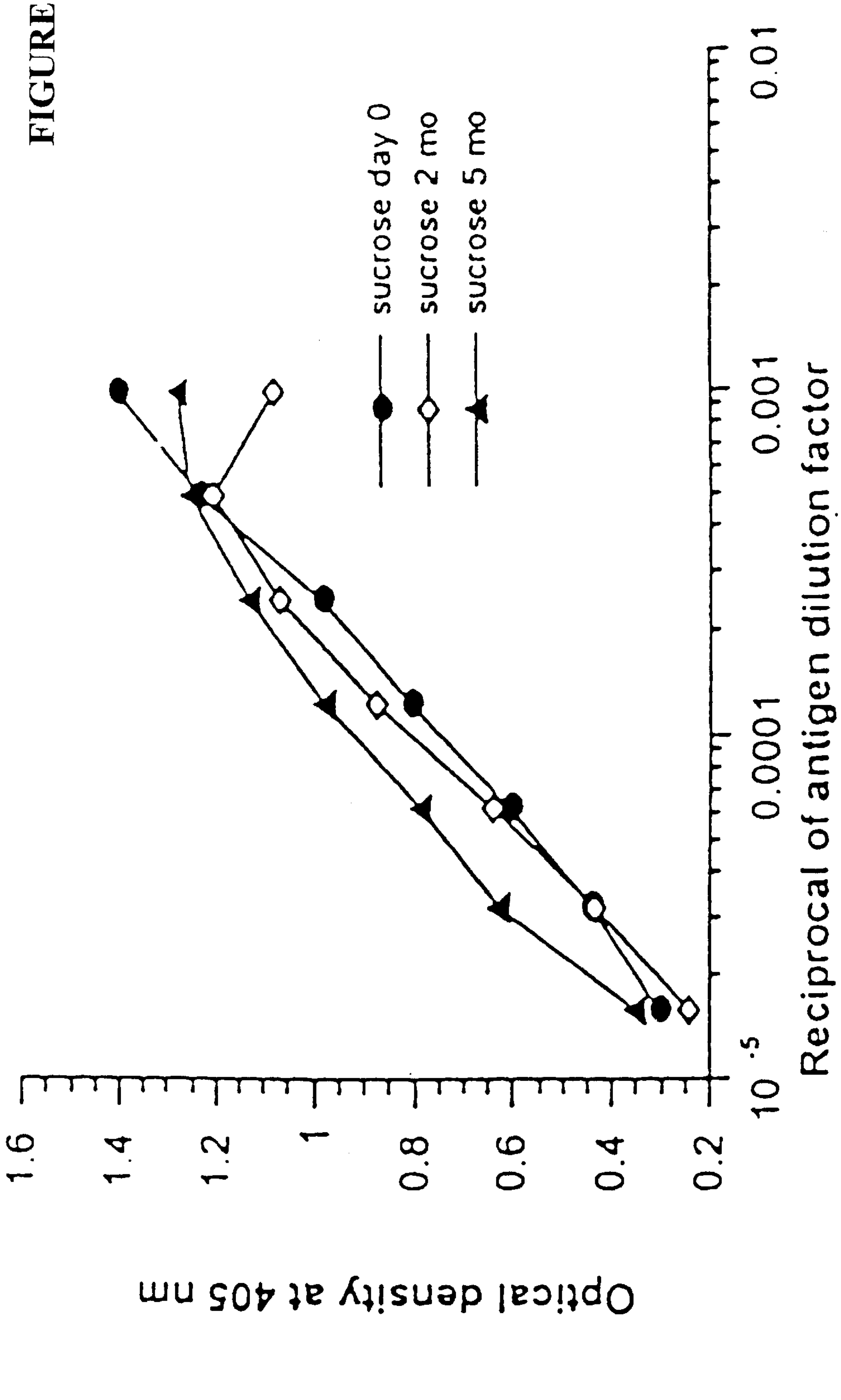
Figure 8C:
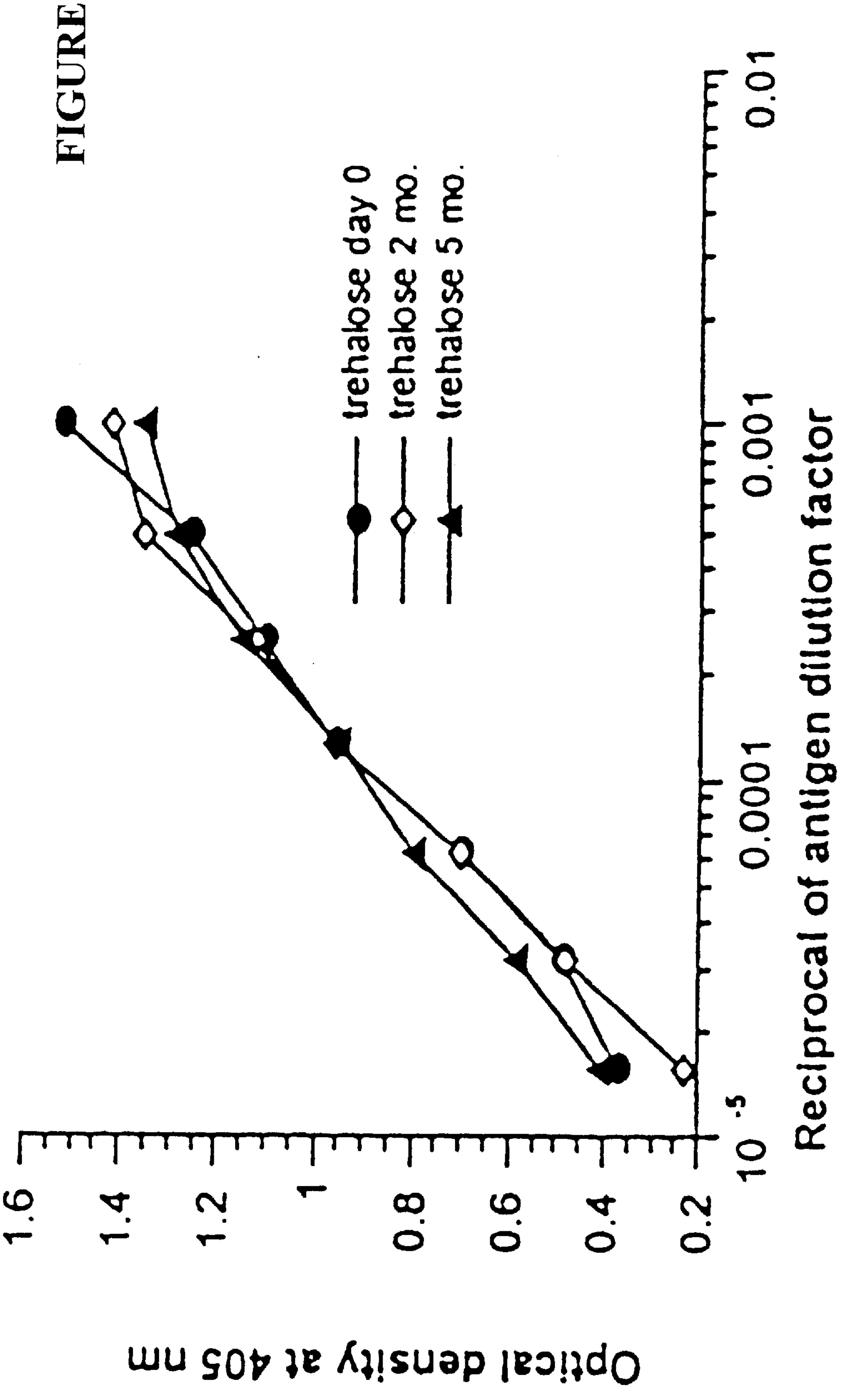

Samples of DEN-2 80E lyophilized with trehalose or sucrose as excipients were dissolved after 2 and 5 months of storage. ELISA (sandwich between 9D12 and E138-2) and SDS-PAGE analysis indicated that no protein degradation or loss of immunoreactivity was evident relative to a sample reconstituted immediately after lyophilization. FIGS. 8A–8C illustrate stability of lyophilized DEN-2 80%E. Several samples were lyophilized from 10 mM phosphate (pH 7.2) containing (8A) no excipient (8B) 5% (w/v) sucrose, or (8C) 5% trehalose. Sandwich ELISA's (9D12 MAb capture, E138-2 anti-domain B rabbit polyclonal detection) were done on samples reconstituted to starting conditions after storage at room temperature for 2 and 5 months; the 'day 0' data correspond to samples lyophilized and reconstituted the next day.

Adult female BALB/c mice (n=5 per group) were immunized subcutaneously with immunoaffinity purified DEN-2 80%E that had been lyophilized from solutions containing the following excipients: sucrose, trehalose, or lactose (method detailed above). One day following lyophilization, antigen samples were reconstituted in PBS and used to immunize mice; each 0.1 ml dose contained 10 gg DEN-2 80%E and 10 μg ISCOMATRIX™ adjuvant Four weeks following the priming dose, mice received a booster injection of freshly reconstituted DEN-2 80%E that had been stored lyophilized at ambient room temperature for one month. DEN-2 80%E stored in PBS at 4° C. served as a positive control. The booster inoculations also contained 10 μg DEN-2 80%E and 10 μg ISCOMATRIX™ per dose. Sera were collected for analysis 10 days after the booster immunization. Although all of the excipients showed a trend towards stabilizing the 80%E antigen, only DEN-2 80%E lyophilized in the presence of lactose showed a statistically significant elevation of neutralizing antibody titers compared to the control antigen stored in the liquid phase ($0.025<p<0.05$). The ELISA and virus neutralizing antibody titers (80% virus plaque reduction, $PRNT_{80}$) are shown in Table 9.

TABLE 9

Serum ELISA and neutralizing antibody titers of mice immunized with reconstituted lyophilized preparations of DEN-2 80% E

| Immunogen | Schedule | Geometric Mean ELISA titer | Geometric Mean $PRNT_{80}$ Titer |
|---|---|---|---|
| IAC-purified DEN-2 80% E Lyophilized with Sucrose ISCOMATRIX ™ adjuvant | 10 μg DEN-2 80% E 10 μg ISCOMATRIX ™ 2x q. 28 days, s.c. | 44572 | 12078 |
| IAC-purified DEN-2 80% E Lyophilized with Trehalose ISCOMATRIX ™ adjuvant | 10 μg DEN-2 80% E 10 μg ISCOMATRIX ™ 2x q. 28 days, s.c. | 25600 | 12023 |
| IAC-purified DEN-2 80% E Lyophilized with lactose ISCOMATRIX ™ adjuvant | 10 μg DEN-2 80% E 10 μg ISCOMATRIX ™ 2x q. 28 days, s.c. | 33779 | 21086 |
| IAC purified DEN-2 80% E liquid ISCOMATRIX ™ adjuvant | 10 μg DEN-2 80% E 10 μg ISCOMATRIX ™ 2x q. 28 days, s.c. | 25600 | 7943 |

In a novel formulation of the recombinant DEN-2 80%E, the immunoaffinity purified 80% product was lyophilized alone and in combination with ISCOMATRIX adjuvant. The reconstituted products were demonstrated to maintain immunogenic potency in mice. Aliquots (200 μl) containing 100 μg of purified DEN-2 80%E in 10 mM sodium phosphate, pH 7.0, were lyophilized with 5% (w/v) lactose excipient. One half of the vials also contained an equivalent amount (100 μg) of ISCOMATRIX adjuvant. The samples were frozen on dry ice-acetone and lyophilized at −33° C. under a pressure of 57 mT for 20 hr. The shelf temperature was then ramped to 25° C. over a period of 400 minutes, in increments of 5° C.×30 min. Samples were dried for 19 hr at 25° C., and sealed under vacuum.

Adult female BALB/c mice were immunized subcutaneously with immunoaffinity purified DEN-2 80%E that had been lyophilized with and without ISCOMATRIX (method detailed above). One day following lyophilization, antigen samples were reconstituted in PBS and used to immunize mice; each 0.1 ml dose contained 10 μg DEN-2 80%E and 10 μg ISCOMATRIX adjuvant. The samples of DEN-2 80%E which were lyophilized without ISCOMATRIX had ISCOMATRIX added at the time of injection. Four weeks following the priming dose, mice received a booster injection of freshly reconstituted DEN-2 80%E, with or without ISCOMATRIX, that had been stored lyophilized at ambient room temperature for one month. The booster inoculations also contained 10 μg DEN-2 80%E and 10 μg ISCOMATRIX per dose. Sera were collected for analysis 10 days after the booster immunization and analyzed for neutralizing antibody responses using the PRNT assays previously described. The results are summarize in Table 10. As is clearly evident from the data, the DEN-2 80%E lyophilized with ISCOMATRIX maintains full immunogenicity compared to DEN-2 80%E in liquid form (See Examples 11,12, 13, and 14) and to DEN-2 80%E lyophilized without ISCOMATRIX. To our knowledge this is the first demonstration of efficacy of a formulation comprised of a recombinant subunit lyophilized with ISCOMATRIX adjuvant.

TABLE 10

[Sera analyzed for neutralizing antibody responses using PRNT assay]

| Immunogen | Schedule | Geometric Mean Neutralizing Antibody Titer (PRNT50) |
|---|---|---|
| IAC-purified DEN-2 80% E Lyophilized with lactose | 10 μg DEN-2 80% E 10 μg ISCOMATRIX ™ 2x q. 28 day, s.c. | 22,265 |
| IAC-purified DEN-2 80% E Lyophilized with lactose and ISCOMATRIX adjuvant | 10 μg DEN-2 80% E 10 μg ISCOMATRIX ™ 2x q. 28 day, s.c. | 34,015 |

What is claimed is:

1. A vaccine comprising an admixture of one or more recombinant flavivirus envelope protein subunits and an immunomodulating agent having an iscom-like structure and comprising within said iscom-like structure at least one lipid and at least one saponin, and a pharmaceutically acceptable vehicle wherein the flavivirus is a dengue virus and wherein at least one of the envelope protein subunits is a portion of the envelope protein (E) that represents the portion of the envelope protein that constitutes 80% of its length starting from amino acid residue 1 at its N-terminus to residue 395 and which portion has been secreted as or is a recombinantly produced protein from Drosophila cells.

2. The vaccine according to claim 1, wherein said at least one lipid is a sterol.

3. The vaccine according to claim 2, wherein said sterol is cholesterol.

4. The vaccine according to claim 1, wherein said at least one saponin is a triterpensaponin.

5. The vaccine according to claim 4, wherein said triterpensaponin is Quil A.

6. The vaccine according to claim 1, wherein the admixture of the recombinant flavivirus envelope proteins subunit (s) and the immunomodulating agent are formulated together and lyophilized as a single entity containing a pharmaceutically acceptable vehicle and excipient.

7. The vaccine according to claim 1, wherein said recombinant flavivirus envelope protein is expressed in *Drosophila melanogaster* Schneider 2 (S2) cell line.

* * * * *